US005575766A

United States Patent [19]
Swartz et al.

[11] Patent Number: 5,575,766
[45] Date of Patent: Nov. 19, 1996

[54] PROCESS FOR THE NONSURGICAL MAPPING AND TREATMENT OF ATRIAL ARRHYTHMIA USING CATHETERS GUIDED BY SHAPED GUIDING INTRODUCERS

[75] Inventors: John F. Swartz, Tulsa, Okla.; John Ockuly, Minneapolis, Minn.

[73] Assignee: Daig Corporation, Minnetonka, Minn.

[21] Appl. No.: 272,014

[22] Filed: Jul. 8, 1994

Related U.S. Application Data

[63] Continuation-in-part of Ser. No. 147,168, Nov. 3, 1993, Pat. No. 5,497,774, and Ser. No. 146,744, Nov. 3, 1993, Pat. No. 5,427,119.

[51] Int. Cl.[6] .................................................. A61M 31/00
[52] U.S. Cl. ............................... 604/53; 607/15; 600/16; 128/702; 128/705
[58] Field of Search ........................... 128/695, 702, 128/705; 604/49, 53, 281; 607/96, 101, 115, 119, 15; 600/15–17

[56] References Cited

U.S. PATENT DOCUMENTS

| | | |
|---|---|---|
| 4,033,031 | 7/1977 | Guss et al. . |
| 4,117,836 | 10/1978 | Erikson . |
| 4,641,649 | 2/1987 | Walinsky et al. . |
| 4,838,879 | 6/1989 | Tanabe et al. . |
| 4,860,769 | 8/1989 | Fogarty et al. ........................ 128/786 |
| 4,882,777 | 11/1989 | Narula ................................... 604/281 |
| 4,883,058 | 11/1989 | Ruiz . |
| 4,898,591 | 2/1990 | Jang et al. . |
| 4,945,912 | 8/1990 | Langberg . |
| 5,016,640 | 5/1991 | Ruiz . |
| 5,104,393 | 4/1992 | Isneri et al. . |
| 5,131,406 | 7/1992 | Kaltenbach ............................ 128/772 |
| 5,147,355 | 9/1992 | Friedman ............................... 606/23 |
| 5,171,232 | 12/1992 | Castillo et al. . |
| 5,188,619 | 2/1993 | Myers . |
| 5,195,942 | 3/1993 | Weil ....................................... 600/16 |
| 5,195,990 | 3/1993 | Weldon . |
| 5,203,776 | 4/1993 | Durfee . |
| 5,209,229 | 5/1993 | Gilli . |
| 5,215,540 | 6/1993 | Anderhub . |
| 5,231,994 | 8/1993 | Harmjanz . |
| 5,290,229 | 3/1994 | Paskar . |
| 5,295,484 | 3/1994 | Marcus ................................... 607/115 |
| 5,299,574 | 4/1994 | Bower . |
| 5,300,106 | 4/1994 | Dahl et al. ............................. 607/119 |
| 5,312,341 | 5/1994 | Turi ......................................... 600/16 |
| 5,366,490 | 11/1994 | Edwards et al. ....................... 607/99 |
| 5,370,678 | 12/1994 | Edwards et al. ....................... 607/101 |
| 5,409,019 | 4/1995 | Wilk ........................................ 600/16 |
| 5,411,531 | 5/1995 | Hill .......................................... 607/14 |
| 5,427,119 | 6/1995 | Swartz .................................... 128/772 |

OTHER PUBLICATIONS

Cox, J. L., et al. "A Review of Surgery for Atrial Fibrillation: J. Cardiovas. Electrophysiology", pp. 541–561 (1990).

Williams, J. M., et al., "Left Atrial Isolation: a new technique for the treatment of superventricular arrhythmias" J. Thoracic Cardiovascular Surgery, pp. 373–380 (1980).

Singer, I., et al. "Catheter Ablation for Arrhythmias" Clinical Manual of Electrophysiology, pp. 421–431 (1993).

Falk, R. H., et al. Atrial Fibrillation Mechanisms and Management, pp. 359–374 (1992).

Horowitz, L. N. Current Management of Arrhythmias pp. 373–378 (1991).

(List continued on next page.)

Primary Examiner—Randall L. Green
Assistant Examiner—Chalin Smith
Attorney, Agent, or Firm—Scott R. Cox

[57] ABSTRACT

A process for the treatment of atrial arrhythmia by use of ablation and/or mapping procedures comprising ablating discrete ablation tracks within the left and right atrium of the heart by use of precurved left and right atrium guiding introducers. Also disclosed are shapes for the guiding introducers to be used for the ablation and/or mapping of the discrete tracks within the left and right atrium.

42 Claims, 15 Drawing Sheets

OTHER PUBLICATIONS

Gallageher, J. J., et al., "Catheter Technique for Closed Chest Ablation of the Atrial Ventricular Conduction System" New England Journal of Medicine, pp. 194–200 (1982).

Tracy, C. M., et al. "Radiofrequency Catheter Ablation of Ectopic Atrial Tachycardia using Paced Activation Sequence Mapping" Journal of American College of Cardiology, pp. 910–917 (1993).

Saul, P. S. et al. "Catheter Ablation of Accessory Ventricular Pathways in Young Patients: Use of Long Vascular Sheaths, the Transseptal Approach and a Retrograde Left Posterior Parallel Approach" J. Amer. Coll. Card. vol. 21, No. 3, pp. 571–583 (1993).

Swartz, J. F., et al. Radiofrequency Endocardial Catheter Ablation of Accessory Pathway Atrial Insertion Sites Circulation, vol. 87, No. 2, pp. 487–99 (1993).

Huang, S. K., et al. "Closed Chest Catheter Desiccation of the Atrio–Ventricular Junction Using Radio Frequency Energy—A New Method of Catheter Ablation" J. Amer. Coll. Card., pp. 349–358 (1987).

Kerr, C., "Atrial Fibrillation: Fact, Controversy and Future" Clinical Progress in Electrophysiology in Pacing, pp. 319, 326–332 (1991).

Heinz, G., et al., "Improvement in Left Ventricular Systolic Function After Successful Radiofrequency His Bundle Ablation for Drug Refractory, Chronic Atrial Fibrillation and Recurrent Atrial Flutter" American Journal of Cardiology, pp. 489–492 (1992).

Guiraudon, G. M., et al., "Combined Sinoatrial Node/Atrio--Ventricular Node Isolation: a Surgical Alternative to His Bundle Ablation in Patients with Atrial Fibrillation" Circulation, vol. 72, (Pt–2) III–220 (1985).

Scheinman, M. M. et al. "Catheter–Induced Ablation of the Atrio–Ventricular Junction to Control Refractory Supraventricular Arrhythmias" JAMA vol. 248, pp. 851–855 (1982).

Cox, J. L., et al., Electrophysiology, Pacing and Arrhythmia, "Operations for Atrial Fibrillation" Clin. Cardiol. vol. 14, pp. 827–834 (1991).

Martin, D., et al., Atrial Fibrillation, pp. 42–59 (1994).

Cox, J. L., et al., "The Surgical Treatment of Atrial Fibrillation" The Journal of Thoracic and Cardiovascular Surgery, vol. 101, No. 4, pp. 406–426, 569–592.

"Anatomy & Physiology" Arthur Ganton, pp. 400, 402.

RIGHT ATRIUM

LEFT ATRIUM

TRACK #1

TRACK #2

TRACK #3

TRACK #4

TRACK #5 - RIGHT ATRIUM

TRACK #6 - RIGHT ATRIUM

TRACK#7 - RIGHT ATRIUM

TRACK#9 - RIGHT ATRIUM

TRACK#8 - INTER CATHETER ABLATION

TRACK#8 - RIGHT ATRIUM

TRACK#8 - LEFT ATRIUM

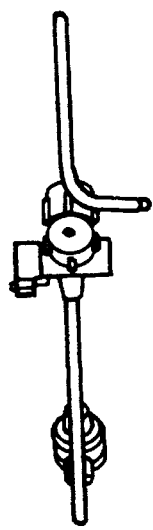
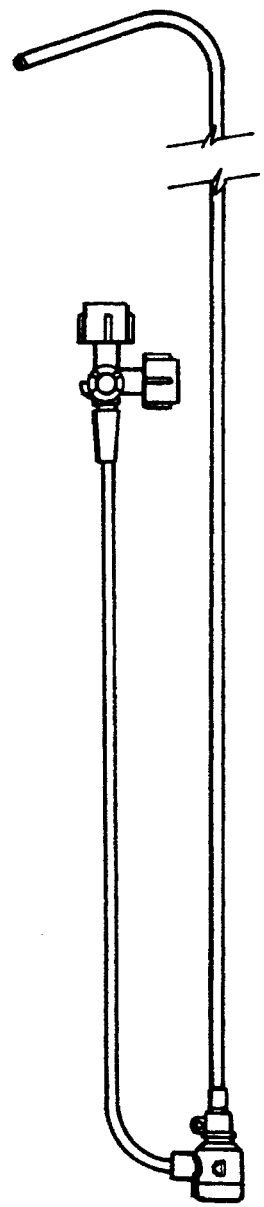
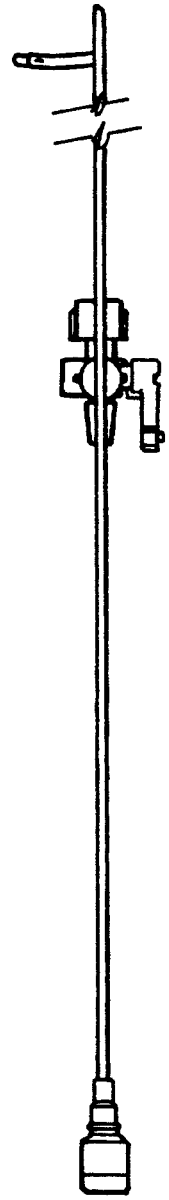
FIG. 7C
FIG. 7A
FIG. 7B

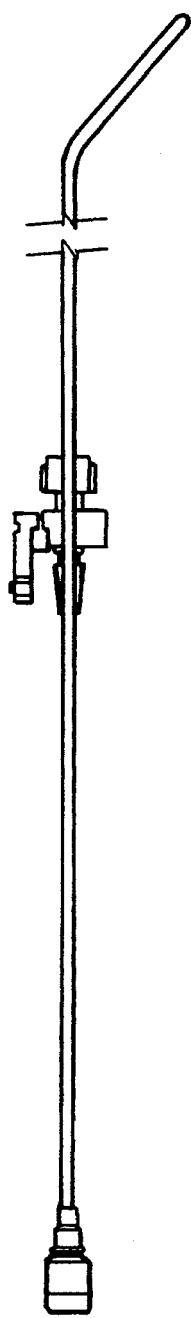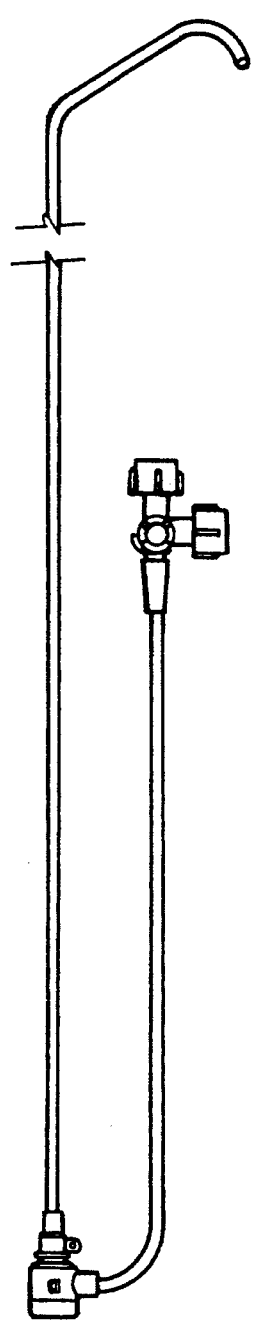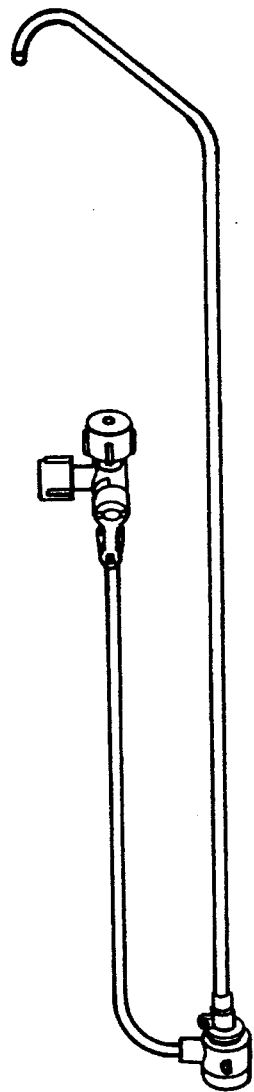
FIG. 11A
FIG. 11B    FIG. 11C

PROCESS FOR THE NONSURGICAL MAPPING AND TREATMENT OF ATRIAL ARRHYTHMIA USING CATHETERS GUIDED BY SHAPED GUIDING INTRODUCERS

CROSS REFERENCE TO RELATED APPLICATIONS

This application is a continuation-in-part of applications Ser. No. 08/147,168, filed Nov. 3, 1993 now U.S. Pat. No. 5,497,774, and Ser. No. 08/146,744, filed Nov. 3, 1993, now U.S. Pat. No. 5,427,119.

BACKGROUND OF THE INVENTION

1. Field of Invention

This invention relates to a process for the mapping and treatment of atrial arrhythmia using catheters guided by shaped guiding introducers. In addition, it relates to the preferred shape of the guiding introducers which are used with a mapping or ablation catheter for the mapping or treatment of atrial arrhythmias.

2. Prior Art

Introducers and catheters have been in use for medical procedures for many years. For example, one use is to convey an electrical stimulus to a selected location within the human body. Another use is to monitor and make measurements for diagnostic tests within the human body. Thus, catheters may examine, diagnose and treat while positioned at a specific location within the body which is otherwise inaccessible without more invasive procedures. In use, catheters may be inserted into a major vein or artery which is near the body surface. These catheters are then guided to a specific location for examination, diagnosis or treatment by manipulating the catheter through the artery or vein of the human body.

Catheters have become increasingly useful in remote and difficult to reach locations within the body. However, the utilization of these catheters is frequently limited because of the need for a precise placement of the electrodes of the catheter at a specific location within the body.

Control of the movement of catheters to achieve such precise placement is difficult because of the inherent structure of the catheter. The body of a conventional catheter is long and tubular. To provide sufficient control of the movement of the catheter, it is necessary that its structure be somewhat rigid. However, the catheter must not be so rigid as to prevent the bending or curving necessary for movement through the vein, artery or other body part to arrive at the specified location. Further, the catheter must not be so rigid as to cause damage to the artery or vein while it is being moved within the body.

While it is important that the catheter not be so rigid as to cause injury, it is also important that there be sufficient rigidity in the catheter to accommodate torque control, i.e., the ability to transmit a twisting force along the length of the catheter. Sufficient torque control enables controlled maneuverability of the catheter by the application of a twisting force at the proximal end of the catheter that is transmitted along the catheter to its distal end. The need for greater torque control often conflicts with the need for reduced rigidity to prevent injury to the body vessel.

Catheters are used increasingly for medical procedures involving the human heart. In these procedures a catheter is typically advanced to the heart through veins or arteries and then is positioned at a specified location within the heart. Typically, the catheter is inserted in an artery or vein in the leg, neck, upper chest or arm of the patient and threaded, often with the aid of a guidewire or introducer, and guided through various arteries or veins until the tip of the catheter reaches the desired location in the heart.

The distal end of a catheter used in such a procedure is sometimes preformed into a desired curvature so that by torquing the catheter about its longitudinal axis, the catheter can be guided to the desired location within the heart or in the arteries or veins associated with the heart. For example, U.S. Pat. No. 4,882,777 discloses a catheter with a complex curvature at its distal end for use in a specific procedure in the right ventricle of a human heart. U.S. Pat. Nos. 5,299,574 and 4,117,836 disclose a catheter for the selective coronary angiography of the left coronary artery and U.S. Pat. Nos. 5,295,574, 5,215,540, 5,016,640 and 4,883,058 disclose catheters for selective coronary angiography of the right coronary artery. See also U.S. Pat. No. 4,033,031. U.S. Pat. No. 5,269,326 discloses a method for transvenously accessing the pericardial space through the right atrium for particular medical procedures. U.S. Pat. No. 4,898,591 discloses a catheter with inner and outer layers containing braided portions. The '591 patent also discloses a number of different curvatures for intravascular catheters. See also U.S. Pat. Nos. 5,231,994, 4,838,879, 5,171,232 and 5,290,229.

Atrial fibrillation is the most common sustained heart arrhythmia. It is estimated to occur in upwards of 0.4 percent of the adult population and perhaps as many as 10 percent of the population who are 60 years or older. Cox, J. L., et al., *Electrophysiology, Pacing and Arrhythmia*, "Operations for Atrial Fibrillation," Clin. Cardiol. 14, 827–834 (1991). Atrial arrhythmia may be transient or persistent. While most atrial arrhythmia occurs in individuals having other forms of underlying heart disease, some atrial arrhythmias occur independently. While atrial arrhythmias do not directly cause death as frequently as ventricular arrhythmias, they increase the risk factor for a number of other diseases such as strokes, thrombosis, atherosclerosis, systemic and cerebral embolism and cause a number of additional medical problems.

In the treatment of atrial fibrillation, antiarrhythmic drugs sometimes provide relief. Anti-arrhythmia drugs are disclosed, for example, in U.S. Pat. Nos. 4,558,155, 4,500,529, 4,988,698, 5,286,866 and 5,215,989. The treatment of atrial arrhythmia by pharmaceutical means has been disclosed in a number of medical articles and books including, for example, Martin, D., et al., *Atrial Fibrillation*, pp. 35–41 (1994); Falk, R. H., et al., *Atrial Fibrillation* (1992); Singer, I., et al., *Clinical Manual of Electrophysiology* (1993); and Horowitz, L. N., *Current Management of Arrhythmias* (1991).

Another treatment for atrial arrhythmia or fibrillation involves the use of an implanted atrial defibrillator or treatments by cardioversion. See, for example, U.S. Pat. Nos. 5,282,836, 5,271,392 and 5,209,229. See also Martin, D., et al., *Atrial Fibrillation.*, pp. 42–59 (1994).

Certain patients with symptomatic or life threatening atrial arrhythmias, however, cannot be adequately treated by drugs or these medical devices. Other forms of aggressive treatment are mandated, which may include surgery. For example, a surgical procedure for the treatment of atrial arrhythmia known as the "Maze" procedure is disclosed in Cox, J. L. et al., *Electrophysiology, Pacing and Arrhythmia*, "Operations for Atrial Fibrillation," Clin. Cardiol. 14, 827–834 (1991). See also Cox, J. L., et al., "The Surgical Treatment of Atrial Fibrillation," *The Journal of Thoracic and Cardiovascular Surgery*, Vol. 101, No. 4, pp. 584–592, 569–583 (April, 1991), and Cox, J. L., et al., "The Surgical Treatment of Atrial Fibrillation," *The Journal of Thoracic and Cardiovascular Surgery*, Vol. 101, No. 4, pp. 406–426 (March, 1991). Other surgical procedures for atrial arrhythmia are disclosed, for example, in Martin, D., et al., *Atrial Fibrillation*, pps. 54–56 (1994).

Another procedure used for certain types of cardiac arrhythmia (but not atrial fibrillation) within the last 10 to 15 years is catheter ablation. This procedure has been used to interrupt or modify existing conduction pathways associated with ventricular arrhythmias within the heart. The particular area for ablation depends on the type of underlying ventricular arrhythmia. One common ablation procedure is for the treatment of atrioventricular (AV) nodal reentrant tachycardia. With this problem ablation of the fast or slow AV nodal pathways has become an accepted treatment. See Singer, I., et al., "Catheter Ablation for Arrhythmias" *Clinical Manual of Electrophysiology*, pp. 421–431 (1993); Falk, R. H., et al., *Atrial Fibrillation Mechanisms in Management*, pp. 359–374 (1992); Horowitz, L. N., *Current Management of Arrhythmias*, pp. 373–378 (1991); and Martin, D., et al., *Atrial Fibrillation*, pp. 42–59 (1994). The use of ablation catheters for ablating locations within the heart has been disclosed, for example in U.S. Pat. Nos. 4,641,649, 5,263,493, 5,231,995, 5,228,442 and 5,281,217. However, none utilize a guiding introducer to guide the ablation catheter to a particular location.

The sources of energy used for catheter ablation vary. Initially, high voltage, direct current (DC) ablation techniques were commonly used. However, because of problems associated with the use of DC current, radio frequency (R.F.) ablation has become a preferred source of energy for the ablation procedures. The use of RF energy for ablation has been disclosed, for example, in U.S. Pat. Nos. 4,945,912, 5,209,229, 5,281,218, 5,242,441, 5,246,438, 5,281,213 and 5,293,868. Other energy sources being considered for ablation of heart tissue include laser, ultrasound, microwave and fulgutronization.

Ablation of a precise location within the heart requires the precise placement of the ablation catheter within the heart. Precisely positioning of the ablation catheter is especially difficult because of the physiology of the heart, particularly as the ablation procedures generally occur while the heart is beating. Commonly, the placement of the catheter is determined by a combination of electrophysiological guidance and fluoroscopy (placement of the catheter in relation to known features of the heart which are marked by radiopaque diagnostic catheters which are placed in or at known anatomical structures such as the coronary sinus, high right atrium and the right ventricle).

While these techniques have been useful for certain arrhythmias, catheter ablation for treatment of atrial fibrillation within the atria has not been disclosed. At best, procedures for ablation of the AV node or the His-Purkinje bundle have been disclosed, for example in U.S. Pat. No. 4,641,649 and Martin, D., et al., *Atrial Fibrillation*, p. 53 (1994).

Accordingly, it is an object of this invention to disclose a process for the mapping and treatment of atrial arrhythmia by the use of ablation catheters guided to a specific location by shaped, guiding introducers.

It is a still further object of this invention to disclose a process for the ablation of defined tracks within the left and/or right atrium as an element of the treatment of atrial arrhythmia.

It is a still further object of the invention to disclose particular shapes for guiding introducers for use with catheters for mapping of the atria and ablation of defined tracks within the left and/or right atrium to treat atrial arrhythmia.

It is a further object of this invention to prepare shaped guiding introducers for use in electrophysiology procedures for the treatment of atrial arrhythmias.

These and other objects can be obtained by the disclosed process for the treatment of atrial arrhythmia and the design of the shaped, guiding introducers for use with that process which are disclosed by the instant invention.

SUMMARY OF INVENTION

The instant invention is a process for the treatment and/or mapping of atrial arrhythmia by the use of mapping and ablation catheters comprising:

introducing into the atria a mapping or ablation catheter placed within a shaped, guiding introducer and mapping or ablating a selected area within the atria.

One preferred embodiment of the invention is a process for the treatment and/or mapping of atrial arrhythmia comprising:

(1) introducing a shaped, guiding introducer into the right atrium of a human heart;

(2) positioning an ablation and/or mapping catheter within the right atrium using the shaped, guiding introducer;

(3) ablating and/or mapping a preselected track within the right atrium by use of the ablation and/or mapping catheter located within the shaped, guiding introducer;

(4) repeating steps (1), (2) and (3) using the same or a different shaped, guiding introducer to ablate and/or map a plurality of preselected tracks within the right atrium, to reduce or eliminate reentry circuits within the right atrium;

(5) introducing a shaped, guiding introducer into the left atrium of a human heart;

(6) positioning an ablation and/or mapping catheter within the left atrium using the shaped, guiding introducer;

(7) ablating and/or mapping a preselected track within the left atrium by use of the ablation catheter located within the shaped, guiding introducer;

(8) repeating steps (5), (6) and (7) using the same or a different shaped, guiding introducer to ablate and/or map a plurality of preselected tracks within the left atrium, to reduce or eliminate reentry circuits within the left atrium; thereby creating a generally uninterrupted pathway or corridor for electrical impulses from the sinoatrial node to the atrioventricular node, while permitting more or less complete atrial contraction and atrioventricular synchrony.

The instant invention also discloses specifically designed shapes for the guiding introducers for use with mapping and/or ablation catheters in the mapping and/or treatment of atrial arrhythmia. In particular, five shaped guiding introducers, each with a different shape, are disclosed for procedures within the left atrium and four shaped guiding introducers are disclosed for procedures within the right atrium.

BRIEF DESCRIPTION OF THE DRAWINGS

FIG. 7A is a first view of the first guiding introducer for the left atrium for use as shown in FIGS. 3A, 3I and 3K to produce track 1 and track 8 in the left atrium with the side port tubing, which is attached to the proximal end of the guiding introducer, directly to the left of the guiding introducer but generally in the same plane thereof.

FIG. 7B is a second view of the first guiding introducer for the left atrium as shown in FIG. 7A rotated 90° counterclockwise such that the guiding introducer is positioned over the side port tubing.

FIG. 7C is a third perspective view of the first guiding introducer for the left atrium rotated 180° from the position of FIG. 7B such that the side port tubing covers a portion of the first guiding introducer.

10A with the side port tubing directly to the right of the guiding introducer and wherein the straight section of the third guiding catheter is generally in the same plane thereof.

Figure 3A:
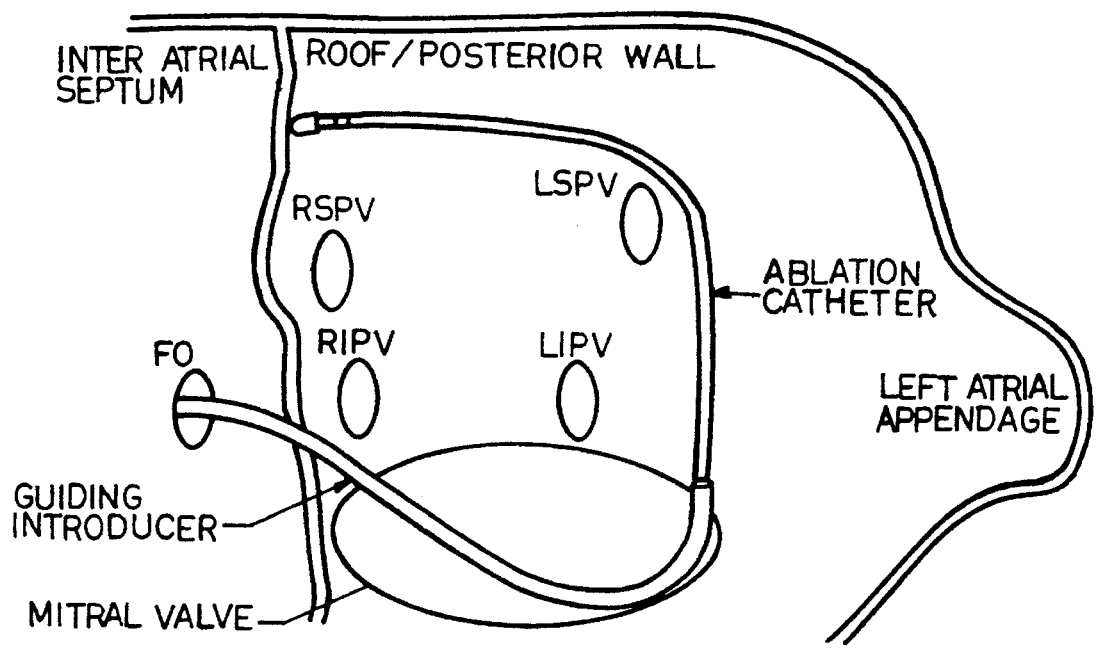
FIG. 3A is a schematic drawing of the left atrium showing the use of the first guiding introducer for the left atrium as shown in FIGS. 7A, B and C to produce track 1.
Figure 3B:
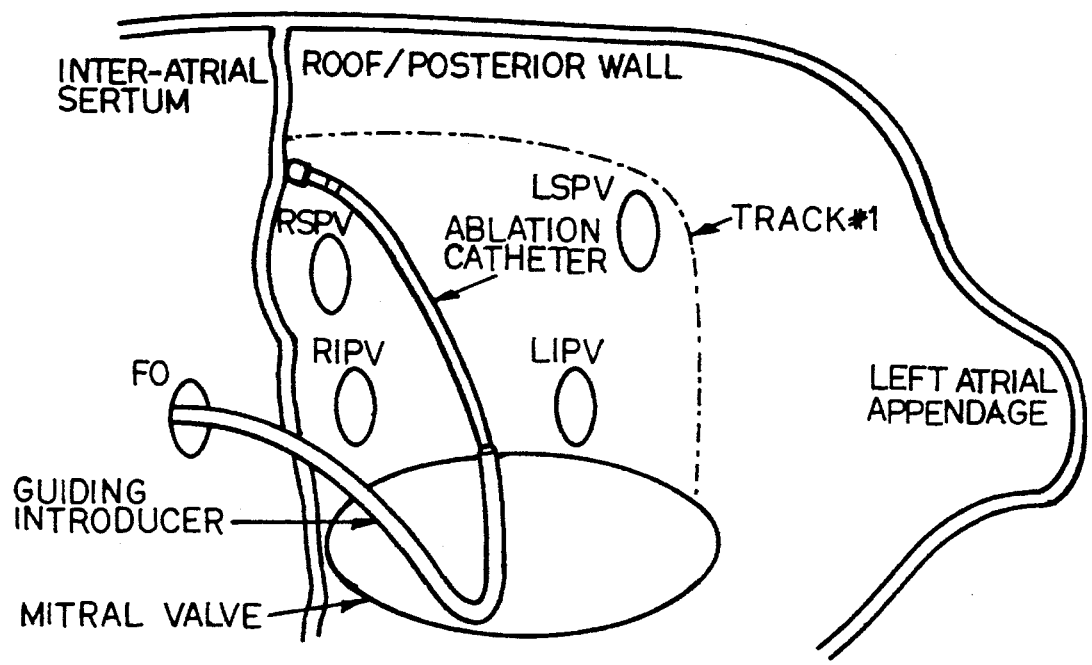
FIG. 3B is a schematic drawing of the left atrium showing the use of the second guiding introducer for the left atrium as shown in FIGS. 9A, B and C to produce track 2.
Figure 3C:
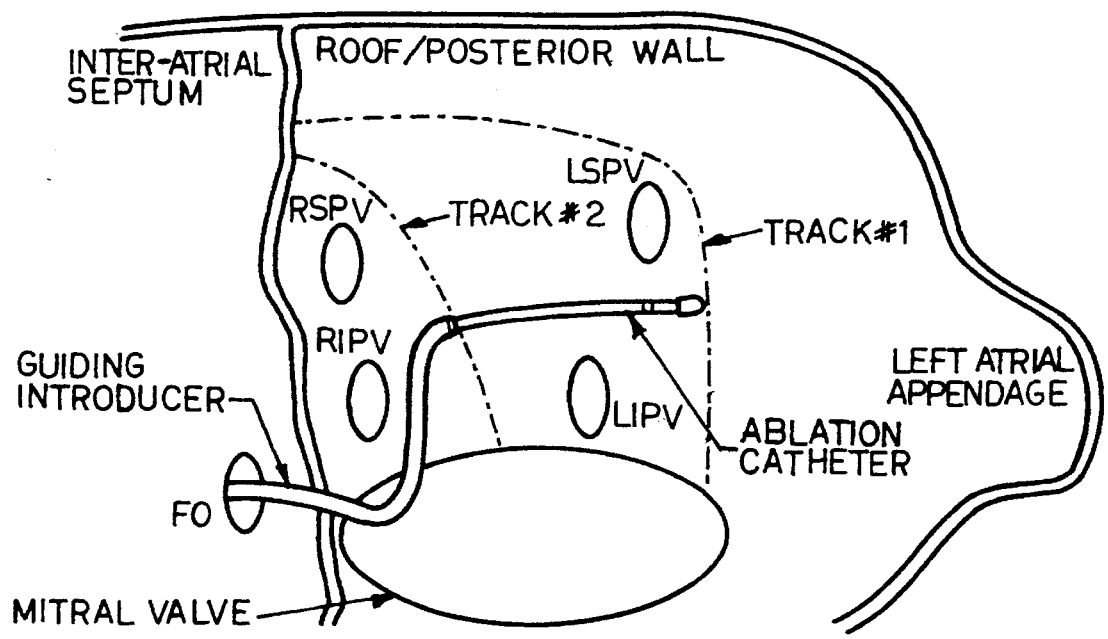
FIG. 3C is a schematic drawing of the left atrium showing the use of the third guiding introducer for the left atrium as shown in FIGS. 10A, B and C to produce track 3.
Figure 3D:
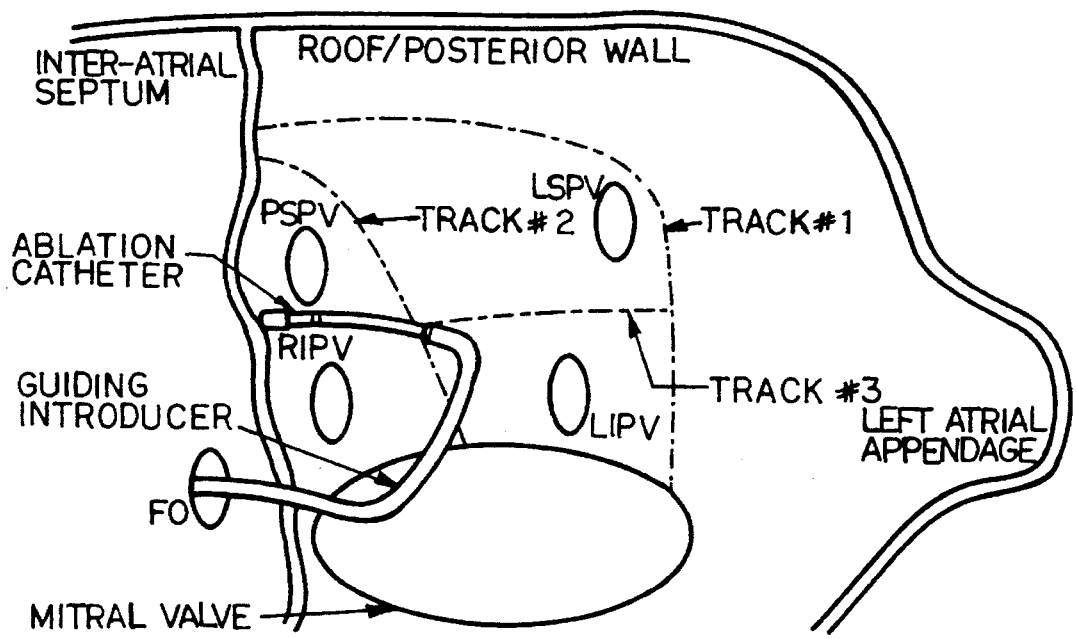
FIG. 3D is a schematic drawing of the left atrium showing the use of the fourth guiding introducer for the left atrium as shown in FIGS. 11A, B and C to produce track 4.
Figure 3E:
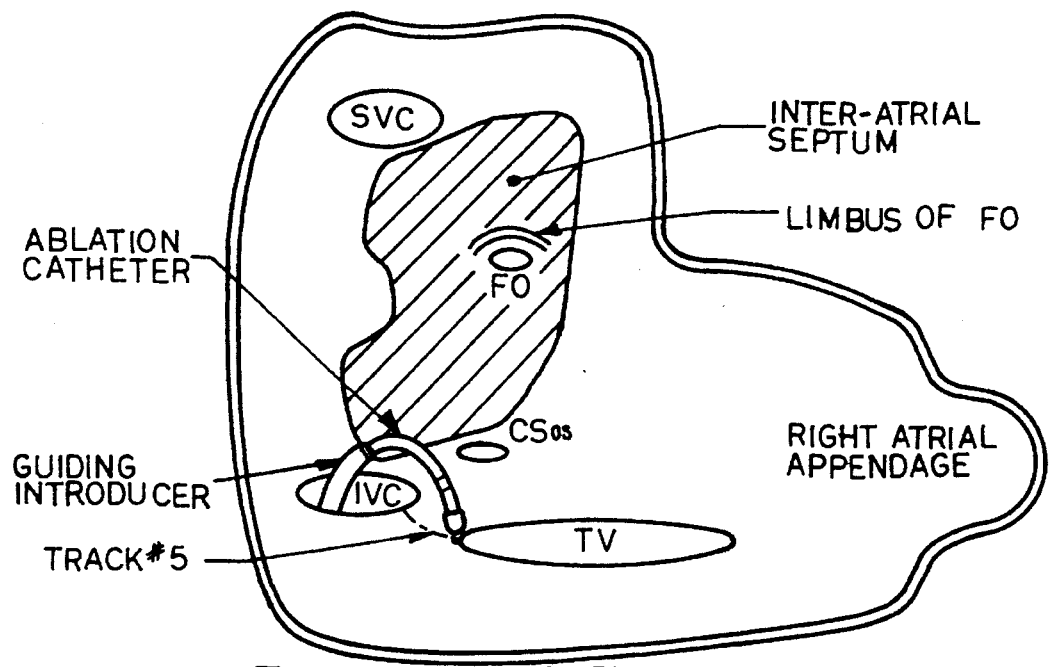
FIG. 3E is a schematic drawing of the right atrium showing the use of the first guiding introducer for the right atrium as shown in FIGS. 5A and B to produce track 5.
Figure 3F:
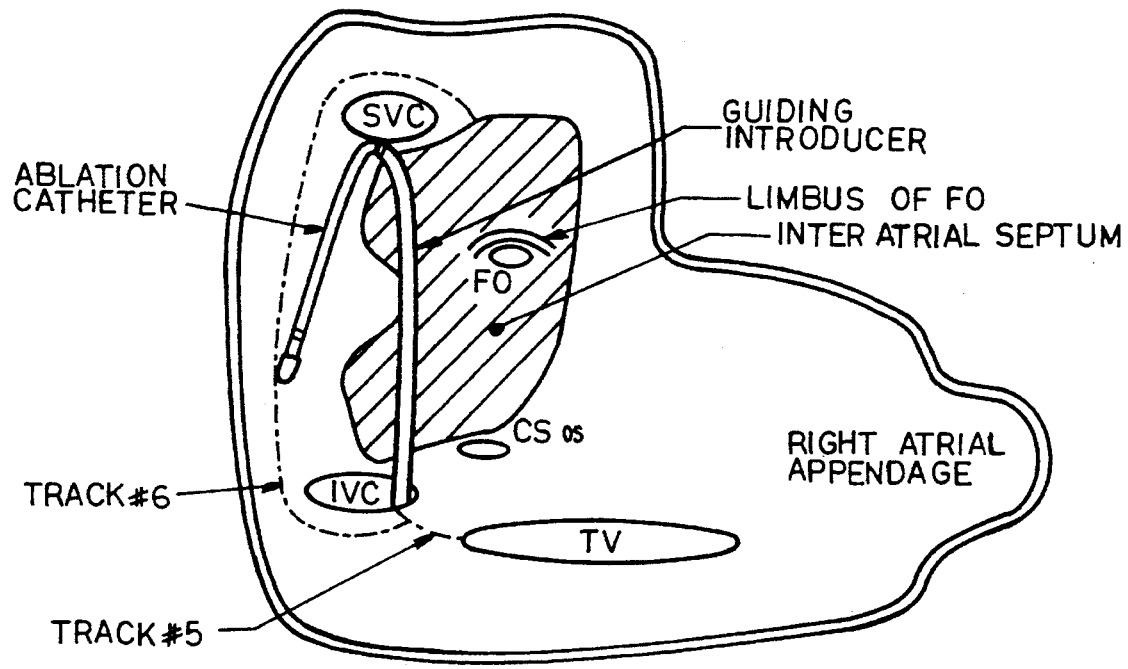
FIG. 3F is a schematic drawing of the right atrium showing the use of the second guiding introducer for the right atrium as shown in FIGS. 6A, B and C to produce track 6.
Figure 3G:
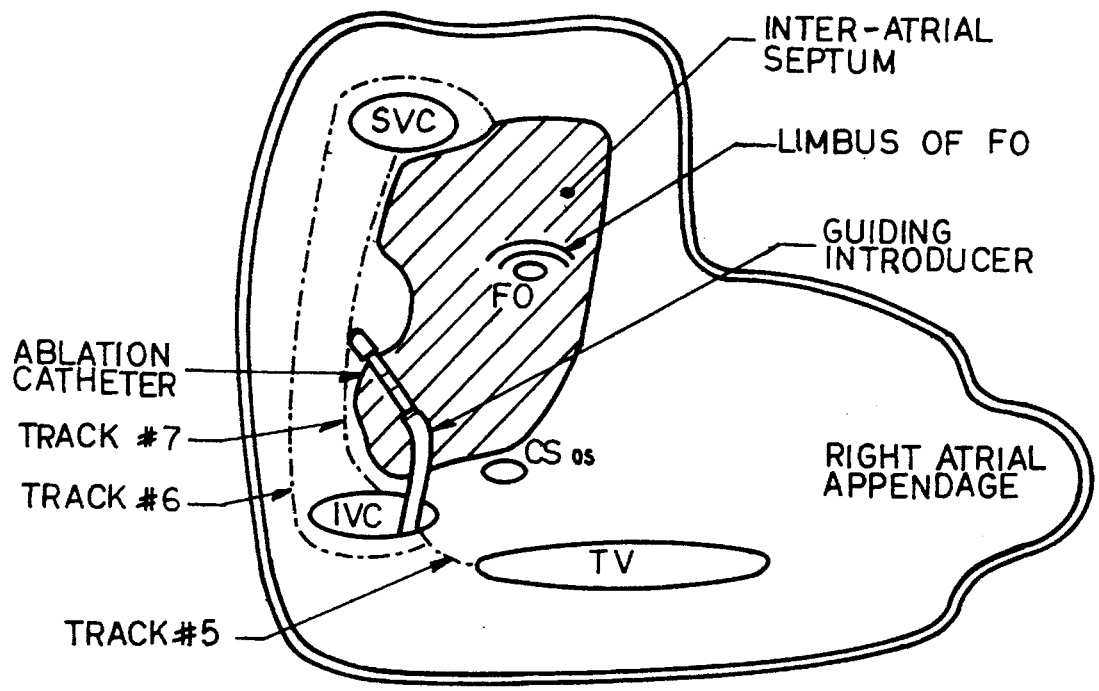
FIG. 3G is a schematic drawing of the right atrium showing the use of the third guiding introducer for the right atrium as shown in FIGS. 4A and B or an alternative use for the second guiding introducer for the right atrium as shown in FIGS. 6A, B and C to produce track 7.
Figure 3H:
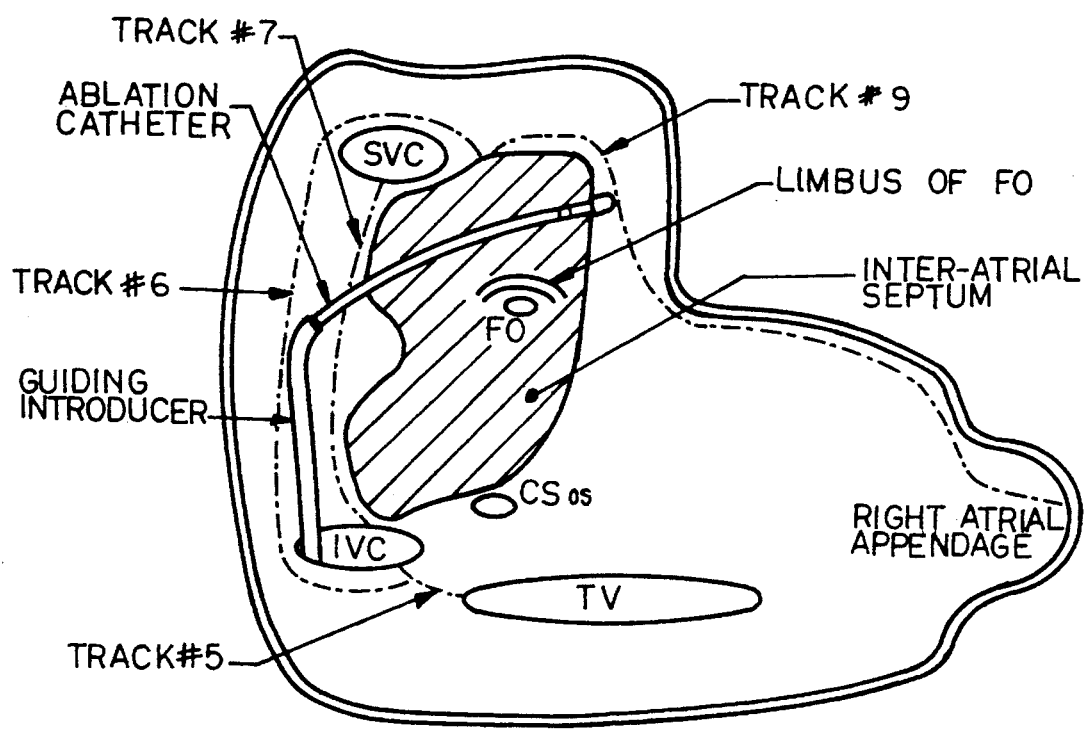
FIG. 3H is a schematic drawing of the right atrium showing the use of the third guiding introducer for the right atrium as shown in FIGS. 4A and B, or an alternative use of the second guiding introducer for the right atrium as shown in FIGS. 6A, B and C, to produce track 9.

FIG. 11A is a first view of the fourth guiding introducer for the left atrium for use as shown in FIG. 3D to produce track 4 with the side port tubing, which is attached to the proximal end of the guiding introducer, directly to the left of the guiding introducer and generally in the same plane thereof.

FIG. 11B is a second view of the fourth guiding introducer for the left atrium rotated 90° counterclockwise from the position of FIG. 11A such that the side port tubing is behind the first section of the fourth guiding introducer.

FIG. 11C is a third view of the fourth guiding introducer for the left atrium rotated 180° from the position shown in FIG. 11A with the side port tubing to the right of the guiding introducer and the straight section of the fourth guiding catheter generally in the same plane thereof.

DETAILED DESCRIPTION OF THE PREFERRED EMBODIMENT

Figure 1:
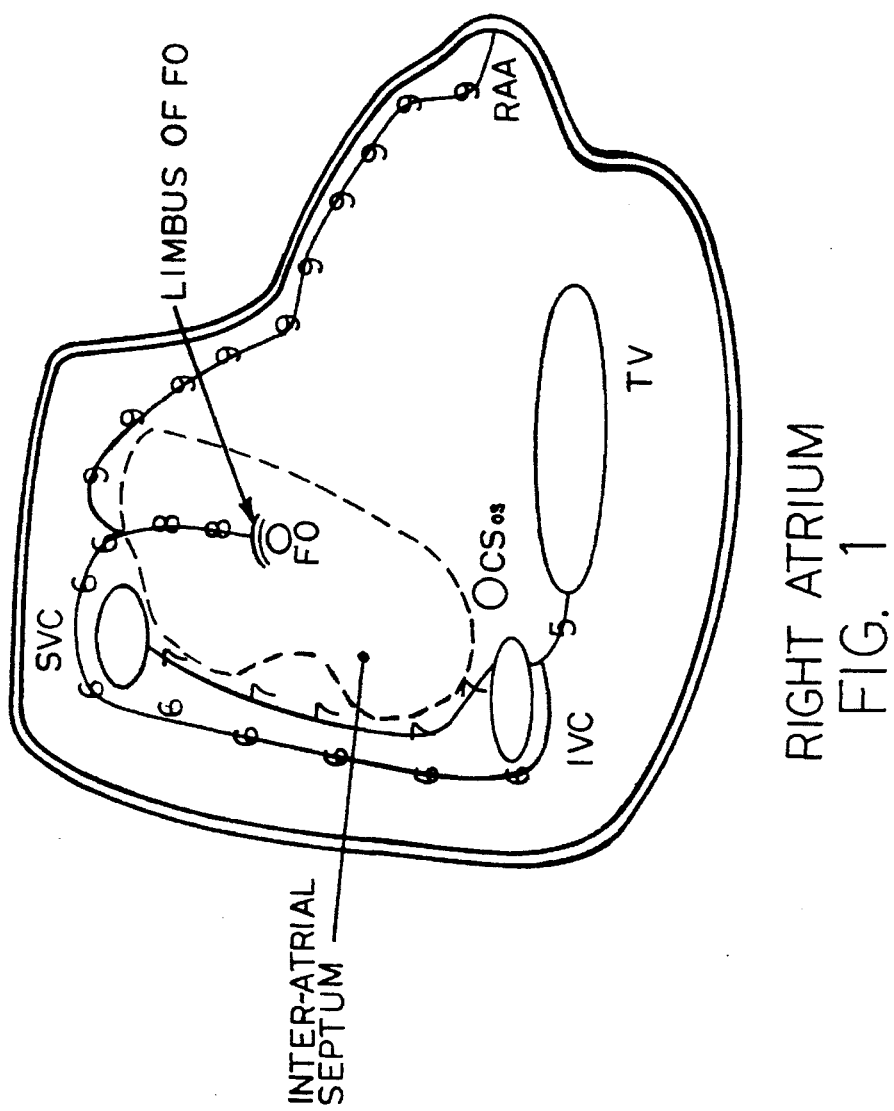
FIG. 1 is a detailed drawing of the right atrium showing the preferred ablation tracks.
Figure 2:
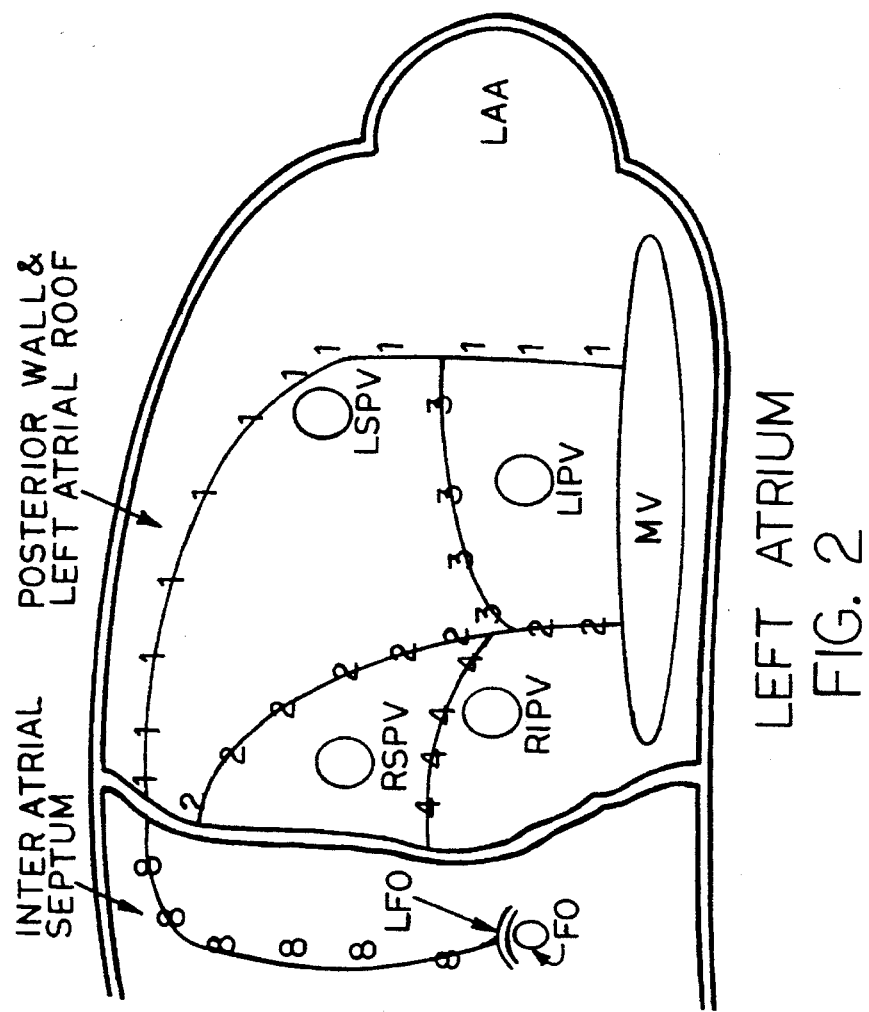
FIG. 2 is a detailed drawing of the left atrium showing the preferred ablation tracks.

A typical human heart includes a right ventricle, a right atrium, left ventricle and left atrium. The right atrium is in fluid communication with the superior vena cava and the inferior vena cava. The atrioventricular septum separates the right atrium from the right ventricle. The tricuspid valve contained within the atrioventricular septum communicates the right atrium with the right ventricle. On the inner wall of the right atrium where it is connected with the left atrium is a thin walled, recessed portion, the fossa ovalis. A detailed schematic drawing of the right atrium is shown in FIG. 1 and a detailed schematic drawing of the left atrium is shown in FIG. 2. In the heart of a fetus, the fossa ovalis is open, (patent foramen) permitting fetal blood to flow between the right and left atria. In most individuals, this opening closes after birth, but in as many as 25 percent of individuals an opening (the patent foramen) still remains in place of the fossa ovalis between the right and left atria. Between the fossa ovalis and the tricuspid valve is the opening or ostium for the coronary sinus. The coronary sinus is the large epicardial vein which accommodates most of the venous blood which drains from the myocardium into the right atrium.

In the normal heart, contraction and relaxation of the heart muscle (myocardium) takes place in an organized fashion as electrochemical signals pass sequentially through the myocardium from the sinoatrial (SA) node to the atrialventricular (AV) node and then along a well defined route which includes the His-Purkinje system into the left and right ventricles. Initial electric impulses are generated at the SA node and conducted to the AV node. The AV node lies near the ostium of the coronary sinus in the interatrial septum in the right atrium. The His-Purkinje system begins at the AV node and follows along the membranous interatrial septum toward the tricuspid valve through the atrioventricular septum and into the membranous interventricular septum. At about the middle of the interventricular septum, the His-Purkinje system splits into right and left branches which straddle the summit of the muscular part of the interventricular septum.

Sometimes abnormal rhythms occur in the atrium which are referred to as atrial arrhythmia. Three of the most common arrhythmia are ectopic atrial tachycardia, atrial fibrillation and atrial flutter. Atrial fibrillation can result in significant patient discomfort and even death because of a number of associated problems, including: (1) an irregular heart rate which causes the patient discomfort and anxiety, (2) loss of synchronous atrioventricular contractions which compromises cardiac hemodynamics resulting in varying levels of congestive heart failure, and (3) stasis of blood flow, which increases the vulnerability to thromboembolism. It is sometimes difficult to isolate a specific pathological cause for the atrial fibrillation although it is believed that the principle mechanism is one or a multitude of reentry circuits within the left and/or right atrium. Efforts to alleviate these problems in the past have included significant usage of pharmacological treatments. While pharmacological treatments are sometimes effective, in some circumstances drug therapy is ineffective and frequently is plagued with side effects such as dizziness, nausea, vision problems and other difficulties.

In the last few years surgical procedures have also been utilized in the treatment of atrial arrhythmia. The goal of these surgical procedures parallel that of the pharmacological treatments, to relieve both the subjective symptoms of atrial arrhythmia as well as to normalize hemodynamics by restoring regular atrial contributions to the cardiac output. One method suggested requires isolation of the left atrium from the remainder of the heart by a surgical procedure. See Cox, J L , et al., "The Surgical Treatment of Atrial Fibrillation," *J. Thoracic and Cardiovascular Surgery*, Vol. 101, No. 4, p. 570 (1991). The initial incisions followed by the scar tissue left by such surgery effectively isolates the left atrium and, in some cases, provides some relief for the patient. Such relief can occur as long as the right atrium maintains adequate sinus rhythm. Various problems associated with this procedure, other than the maintenance of appropriate sinus rhythm, include thromboembolic risks.

Another procedure for treatment of atrial arrhythmia involves the ablating of the His bundle. A permanent pacemaker is then installed, resulting in a regular ventricular beat. See Cox, J. L., et al , The Surgical Treatment of Atrial Fibrillation," *Journal of Thoracic and Cardiovascular Surgery*, Vol. 101, No. 4, pp. 570–572 (1991). However, because the atria may continue to fibrillate, normal cardiac hemodynamics are not restored and there is still vulnerability to thromboembolism.

A newer surgical procedure designed by Guiraudon in 1985 results in the creation of a narrow corridor between the SA node and the AV node. See Guiraudon, G. M., et al, *Combined Sinoatrial Node/Atrial Ventricular Node Isolation: a Surgical Alternative to His Bundle Ablation in Patients with Atrial Fibrillation;* Circulation 72: (pt-2) III-220 (1985). This procedure isolates a narrow corridor from the remainder of the atrial muscle tissue and can, in some circumstances, alleviate some of the problems associated with the atrial arrhythmia.

A more recent, more complex surgical procedure, the "Maze" procedure, has also been designed to treat atrial arrhythmia. See Cox, J. L., et al., "The Surgical Treatment of Atrial Fibrillation," *Journal of Thoracic and Cardiovascular Surgery*, Vol 101 pp. 569–83 (1989). Appropriately placed atrial incisions are designed to interrupt the conduction routes of those areas in the atria that produce the most common reentrant circuits. The procedure is also designed to direct the sinus impulse from the sinus node to the AV node along a specified route. After the procedure, the entire atrial myocardium (except for the atrial appendages and pulmonary veins) is designed to be electrically active by providing for multiple blind alleys off the main conduction route between the SA node and the AV node, thereby preserving atrial transport function postoperatively. While this procedure has resulted in successful treatments for certain patients, there are significant potential risks due to the extensive nature of the surgery."

The effectiveness of the "Maze" procedure is dependent upon the destruction of tissue within the atrium along specific lines or tracks to prevent the formation of reentry circuits while still allowing the atria to contract and permitting the return of normal atrio-ventricular conductivity. It has been discovered that similar success can be achieved without invasive surgery by the use of ablation procedures performed within the atria. However, to accomplish this procedure the ablation catheter must be positioned at predetermined locations within the right and left atrium to ablate predetermined tracks within the left and right atria, thus forming a natural barrier to the formation of the reentry circuits. In addition to the necessity of producing ablation tracks in well defined areas of the left and right atria, it is also critical for proper transmural lesion formation that adequate contact pressure be maintained between the ablation catheter electrode and the heart tissue to be ablated.

The ablation catheters used to perform the ablation procedures produce scar tissue at the selected site within the atria. The energy necessary to scar or ablate the tissue can be provided by a number of different sources. Originally direct current was utilized to provide the energy for ablation procedures. More recently the preferred choice of energy source has been radio frequency energy (R.F.). Laser, microwave, ultrasound and fulgutronization procedures have also been utilized to perform ablation procedures. The preferred source of energy for the ablation procedures of the instant invention is RF energy.

One of the significant difficulties to performing any cardiac procedure in the atria is caused by the physiology of the atria themselves when beating, especially if that beating is abnormal. The preferred procedure for the creation of ablation tracks within the left and right atria thus requires the precise positioning and contact pressure of the ablation catheter within the atria to ablate a predetermined track in the tissue of the atria. These lesions or tracks may be in the same locations as the incisions in the "Maze" procedure, but may also be positioned at different locations within the atria to produce similar results.

Mere introduction of an ablation catheter into either the left or right atrium without precise placement and precise contact pressure will not be sufficient to allow the creation of the desired ablation tracks. This precise placement and contact pressure cannot be produced without the use of specialized precurved guiding introducers to guide the ablation catheter to the correct location and to permit adequate pressure to be placed on the tip of the ablation catheter to produce an adequately ablated track.

An element of treatment of atrial arrhythmia also includes sensing of locations in the atria to efficiently and accurately map the atria. The physiology of the heart and its beating also interferes with the effectiveness of mapping catheters. The guiding introducers of the instant invention can also assist in the precise placement of these mapping catheters.

Medical practitioners often monitor the introduction of cardiac catheters and their progress through the vascular system by use of fluoroscopes. Unfortunately, fluoroscopes can not easily identify specific features in the heart, in general, and the critically important structures of the right and left atrium in specific, thus making placement and utilization of an ablation catheter extremely difficult without a curved, guiding introducer. This placement is especially difficult as the beating heart is in motion, resulting in the catheter moving within the atria as blood is being pumped through the heart. The structure and shape of the guiding introducers of the instant invention addresses and solves these problems and permits the precise placement necessary for accurate ablation procedures.

The shaped guiding introducers position the mapping and/or ablation catheter at the precise location necessary for the procedure automatically as a result of their shapes. The specially designed guiding introducers are produced from conventional elongated catheters. Although these guiding introducers are described as having multiple sections, preferably, they are produced by a conventional introducer production procedure, formed into a single unitary structure. Additional features of these guiding introducers other than their unique shape include radiopaque tip markers and vents which will be discussed in more detail later.

Although in the preferred embodiment a single guiding introducer is used to assist the ablation catheter in ablating a particular track within either the left or the right atrium, alternatively a pair or more guiding introducers may be used in combination to create the appropriate shaped guiding introducers. For example, a first shaped guiding introducer may be placed within a second shaped guiding introducer wherein the combination of the shape of the first and second guiding introducers operating together will create a plurality of different shapes depending upon the rotation of the first and second guiding introducer and the extent of the extension of the inner guiding introducer within the outer guiding introducer.

Where a single guiding introducer is used for each procedure, each of the guiding introducers are used independently to guide the catheter along a separate track or tracks. With the precurved, guiding introducer holding the ablation catheter in a predetermined location, the ablation catheter then ablates a predetermined ablation track. More than one passage over a track may be necessary to fully ablate the track. Sensing elements within the catheter also can be used to sense activity along the track. After the ablation procedure is complete, this first shaped guiding introducer is removed and a second shaped guiding introducer is inserted in place thereof and the procedure is repeated with the ablation catheter to create the next ablation track. This procedure is then continued until there has been a full and completion ablation of all preselected ablation tracks in the heart. The choice of which shaped catheter to use first and in what order is, of course, determined by the individual medical practitioner.

The choice of the selected tracks within the left and right atrium is determined generally from previous experimental and clinical data which has been gathered on the subject. See, for example, Cox, J. L., et al., "The Surgical Treatment of Atrial Fibrillation" *J. Thoracic Cardiovasc. Surg.*, 101:406–426 (1991). However, adjustment in the location of the ablation tracks and the number of tracks is clearly within the discretion of the medical practitioner. For example, the medical practitioner may choose to isolate completely the left atrium as suggested by Scheinman in *Catheter-Induced Ablation of the Atrioventricular Junction to Control Refractory Supraventricular Arrhythmias*, JAMA 248: 851–5 (1982). Alternatively, the medical practitioner may choose to form a "corridor" between the sino-atrial node and the AV node as suggested by Guiraudon in Guiraudon, G. M., et al., *Combined Sino-Atrial Node Atria-ventricular node isolation: A Surgical Alternative to His Bundle Ablation in Patients with Atrial Fibrillation*, 72 (Pt 2); III 220 (1985).

While the ablation and mapping procedures may commence either in the left or right atrium first, preferably, the procedures begin in the right atrium, prior to breach of the interatrial septum. The ablation procedures in the right atrium are designed specifically to prevent the development of or to retard existing atrial flutter. They may also assist in the treatment of other atrial arrhthymia. The ablation tracks for the right atrium are designed to eliminate reentry circuits from forming, particularly around the superior vena cava, the inferior vena cave and the right atrial appendage. FIG. 1 shows a schematic drawing of the preferred ablation tracks within the right atrium listed as tracks 5, 6, 7, 8 and 9. Fewer or more ablation tracks may be created depending on the choice of the medical practitioner. The choice as to which tracks are done first is also left to the discretion of the medical practitioner.

Figure 3I:
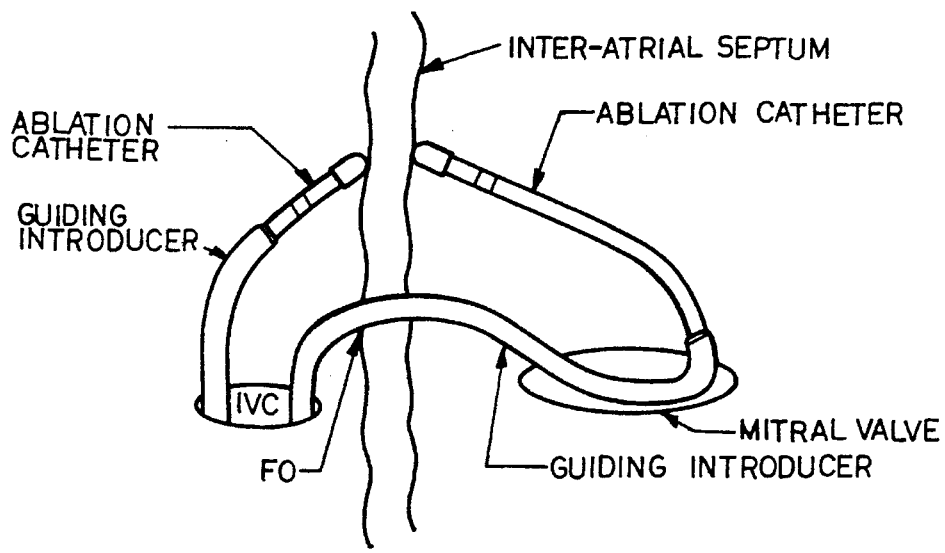
FIG. 3I is a schematic drawing of the interatrial septum showing the use of guiding introducers for simultaneous ablation in the left and right atrium as shown in FIGS. 4A and B for the right atrium and FIGS. 7A, B and C or, alternatively, FIGS. 8A and B, for the left atrium to produce the two parallel tracks designated as track 8.
Figure 3J:
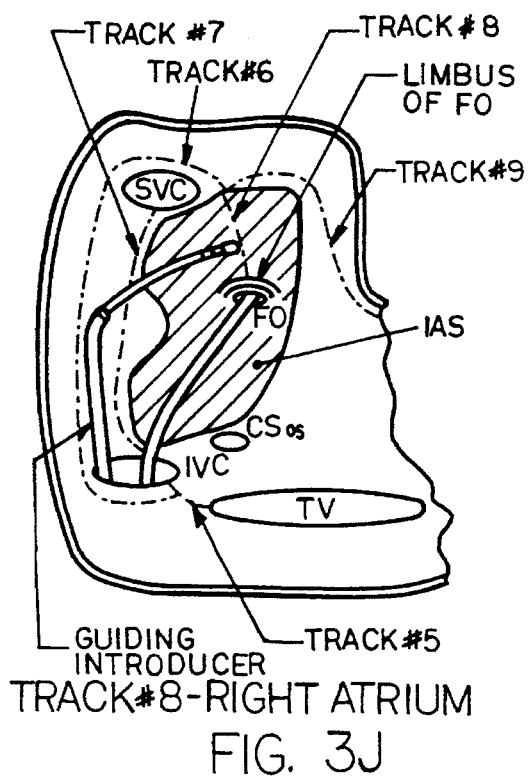
FIG. 3J is a schematic drawing of the right atrium showing the use of the guiding introducers in FIGS. 4A and B to produce track 8 in the right atrium.
Figure 3K:
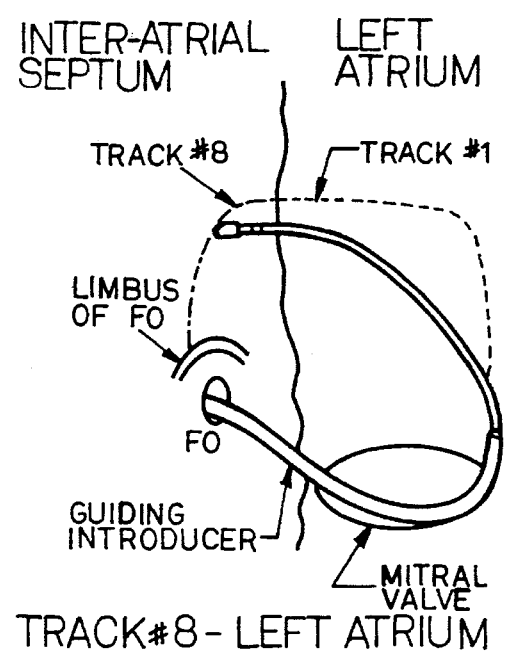
FIG. 3K is a schematic drawing of the left atrium showing the use of one of the guiding introducers used in FIG. 3I in the left atrium, as shown in FIGS. 7A, B and C, or an alternative use of the guiding introducer shown in FIGS. 8A and B, to produce track 8 in the left atrium.

The ablation track in the interatrial septum in the right atrium designated as track 8 is preferably produced at the same time that a corresponding ablation track in the interatrial septum in the left atrium is produced. See FIG. 1, track 8, FIG. 2, track 8 and FIGS. 3I, 3J and 3K. The preferred procedure for producing these particular ablation tracks uses intercatheter ablation techniques, one catheter using a particularly preferred guiding catheter for use in the left atrium and a second catheter using a particularly preferred guiding introducer to perform the ablation procedure along the interatrial septum in the right atrium. The track runs from the limbus of the fossa ovalis, superior to the septal roof to join the track produced by the first guiding introducer for the left atrium (FIG. 2, track 1) and FIG. 1, track 6 in the right atrium. This is possible because the track in the left atrium and that in the right atrium are on either side of the interatrial septum. Preferably these tracks are produced after the remaining right side tracks are produced.

Figure 4B:
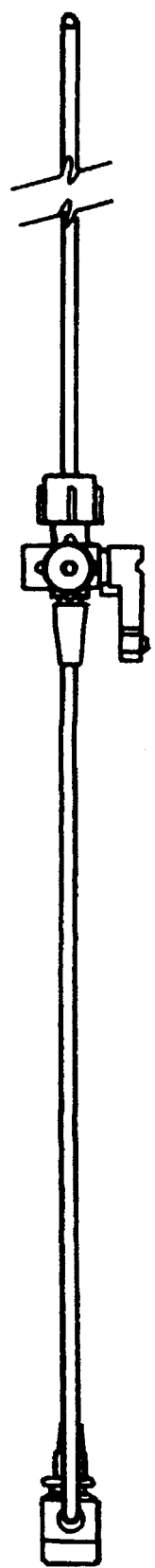
FIG. 4B is a second view of the first guiding introducer for the right atrium rotated 90° clockwise from the position of FIG. 4A such that the side port tubing is positioned over a portion of the first section of the first guiding introducer.
Figure 4A:
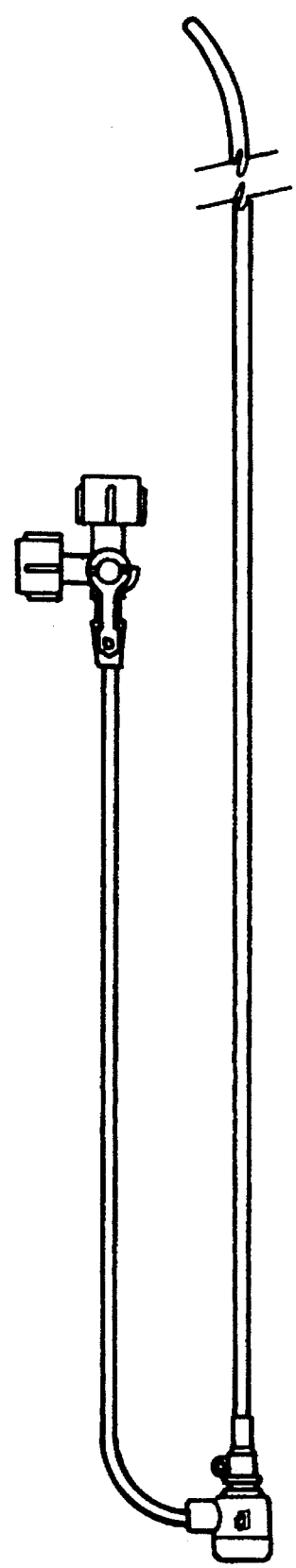
FIG. 4A is a first view of the first guiding introducer for the right atrium as used in FIGS. 3G, 3I and 3J to produce track 7 and track 8 in the right atrium with the side port tubing, which is attached to the proximal end of the guiding introducer, directly to the left of the guiding introducer but generally in the same plane thereof.

While no specifically shaped guiding introducer is necessary for this procedure in the right atrium, as it can be done using conventional fluoroscope techniques, a guiding introducer with the minimal curve is preferably used to guide the catheter along track 8 in the right atrium. See FIG. 1. The guiding introducer to produce this track within the right atrium is preferably divided into two sections. Each section is preferably merged with the remaining section to form a continuous guiding introducer, preferably formed in a single production process. See FIGS. 4A and 4B and FIGS. 3I and 3J. This guiding introducer is the same guiding introducer disclosed in FIG. 2 of copending application 08/146,744 assigned to a common assignee. The first section of this guiding introducer is a conventional, generally elongated hollow straight introducer section of sufficient length for introduction into the patient and for manipulation from the point of insertion to the specific desired location within the right atrium of the heart. Merged with the distal end of the first section of this guiding introducer is a second section which is comprised of a curved section curving to the left as shown in FIG. 4A. The angle of this curve is from about 45° to about 55° and preferably about 60°. The radius of the curve is from about 0.50 to about 2.00 in. and preferably from 1.00 to about 2.00 in. The overall length of this curved section is from about 0.20 to about 2.00 in. and preferably from about 0.50 to about 1.00 in. The third section of the guiding introducer is merged with the distal end of the second section. The third section is comprised of a generally straight section directed at an angle of about 40° to about 60° from the direction of the first section as shown in FIG. 4A and has an overall length of about 0.50 in. to about 3.00 cm.

The ablation track of the left atrium which is produced at the same time as the ablation track for the right atrium, shown as track 8 on FIG. 2, is made beginning at the limbus of the fossa ovalis superior to the septal roof to join track number 1 shown on FIG. 2. This track is also designated as track 8 on FIG. 3K. The guiding introducer used to produce this track within the left atrium is shown in FIGS. 7A, 7B and 7C. The first section of the first guiding introducer is a conventional, generally elongated hollow, straight section of sufficient length for introduction into the patient and for manipulation from the point of insertion to the specific desired location within the left atrium of the heart. Merged with the distal end of the first section of the first shaped guiding introducer is the second section which is comprised of a curved section and a straight section. The curved section is curved to the left when placed in the position shown in FIG. 7A. The inner angle of this curve is from about 60° to about 80° and more preferably from about 65° to about 75°. The radius of this curve is from about 0.30 in. to about 0.70 in. and preferably from about 0.40 in. to about 0.60 in. At the end of this curve is the straight section which is from about 0.40 to about 1.00 in. in length and preferably from about 0.40 to about 0.85 in. The third section of this first shaped, guiding introducer is merged with the distal end of the straight section of the second section. The third section is comprised of a curved section and a straight section. The curved section curves backward in relation to the first section as shown in FIG. 7A at an angle of about 80° to about 100° as shown in FIGS. 7B and 7C and preferably from about 85° to about 95° with a radius of about 0.20 in. to about 0.40 in. and preferably from about 0.25 to about 0.35 in. At the end of this curve is the final straight section whose length is from about 0.25 to about 0.65 in. and preferably from about 0.40 to about 0.50 in., ending in the distal tip of the catheter.

Figure 8A:
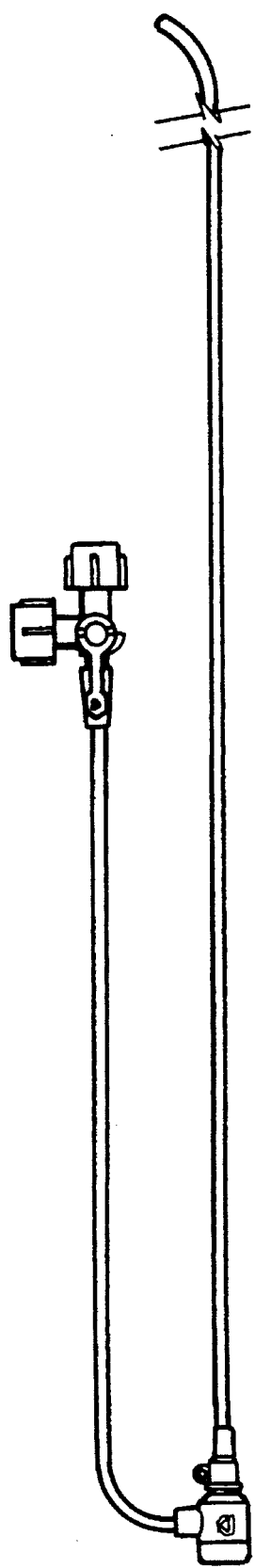
FIG. 8A is the first view of an alternative guiding introducer for the left atrium to that shown in FIGS. 7A, 7B and 7C for use as shown in FIGS. 3I and 3K to produce track 8 in the left atrium with the side port tubing, which is attached to the proximal end of the guiding introducer, directly to the left of the guiding introducer and generally in the same plane thereof.
Figure 8B:
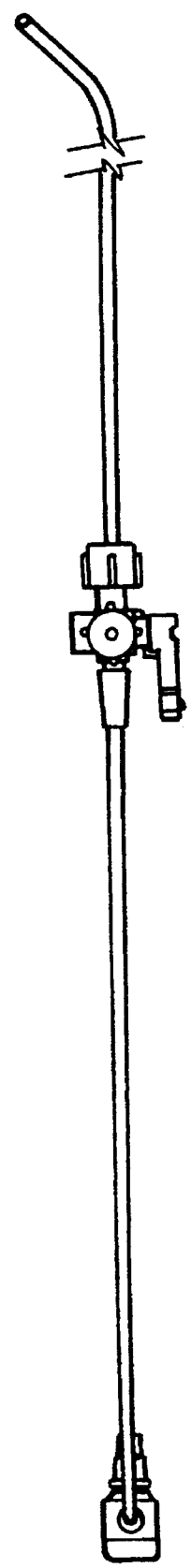
FIG. 8B is the second view of the guiding introducer for the left atrium as shown in FIG. 8A rotated 90° clockwise such that the side port tubing covers a portion of the first portion of the guiding introducer.

Alternatively, to produce track 8 in the left atrium, the guiding introducer as disclosed in copending application Ser. No. 08/147,168, FIG. 3 (assigned to a common assignee) may be used. This guiding introducer is comprised of a first, second and third section. See FIGS. 8A and 8B. The first section is a conventional, generally elongated hollow, straight introducer section of sufficient length for introduction into the patient and for manipulation from the point of insertion to the specific desired location within the heart. Merged with the distal end of the first section of the sheath is the second section which is curved in a compound curve curving first upward in a first longitudinal curve and simultaneously curving to the left in a second longitudinal curve. The first longitudinal curve has a radius of from about 0.50 in. to about 2.00 in. and preferably from about 0.50 cm. to about 1.50 in. The arc of the first longitudinal curve is preferably from about 40° to about 60° and more preferably from about 45° to about 55°. The second longitudinal curve of the second section contains a radius from about 0.50 in. to about 4.00 in. and preferably from about 0.50 in. to about 2.00 in. The third section of the guiding introducer is a third longitudinal curve wherein the plane of the third section is angled upward at an angle of approximately 40° to about 60° and preferably about 45° to about 55° wherein substantially all of said third section co-planar (at least within 15° coplanar). The arc of this longitudinally curved section of the third section has an arc of about 35° to about 55°, preferably from 40° to about 50°.

The distal tip of all guiding introducers may be, and preferably will be, tapered to form a good transition with a dilator. This tapering is preferably less than 10° and more preferably about 4° to about 7°. The guiding introducers preferably may also contain one or a multitude of radiopaque tip marker bands near the distal tip of the introducer. These guiding introducers also preferably contain one or a plurality of vents near the distal tip of the guiding introducer, preferably three or four such vents. The vents are preferably located no more than about 1.00 in. from the tip of the guiding introducer and more preferably 0.10 to about 1.00 in. from the tip. The size of these vents should be in the range of about 40 to about 60/1000 of an inch in diameter. These vents are generally designed to prevent air embolisms from entering the guiding introducer caused by the withdrawal of the catheter contained within the guiding introducer in the event the distal end of the guiding introducer is occluded. For example, if the tip of the guiding introducer is placed against the myocardium and the catheter located within the guiding introducer is withdrawn, a vacuum may be created within the guiding introducer if no vents are provided. If such vacuum is formed, air may be forced back into the guiding introducer by the reintroduction of the catheter into the lumen of the guiding introducer. Such air embolisms could cause significant problems in the patient, including the possibility of a stroke, heart attack or other such problems common with air embolisms in the heart. The addition of vents near the distal tip of the guiding introducer prevents the formation of such vacuum by permitting fluid, presumably blood, to be drawn into the lumen of the guiding introducer as the catheter is being removed from the guiding introducer, thus preventing the possibility of formation of air embolisms within the guiding introducer.

The guiding introducers may be made of any material suitable for use in humans which has a memory or permits distortion from, and substantial return to, the desired three dimensional or complex multiplanar shape. For the purpose of illustration and not limitation, the internal diameter of the guiding introducer may vary from about 6 to about 10 "French" (1 French equals ⅓ of a millimeter). Such guiding introducer can accept dilators from about 6 to about 10 French and appropriate guidewires. Obviously, if larger or smaller dilators or catheters are used in conjunction with the guiding introducers of the instant invention, modifications in size or shape can be made to the instant guiding introducers.

Variations in size and shape of the guiding introducers are also intended to encompass pediatric uses for the guiding introducers of the instant invention, although the preferred uses are for adult human hearts. It is well recognized that pediatric uses may require reductions in size of the various sections of the guiding introducer, in particular the first section, but without any significant modification to the shape or curve of the guiding introducer.

In addition, variations in size or shape of the guiding introducers are also intended to encompass the specialized situations that sometimes occur in patients with enlarged and rotated hearts.

Figure 5B:
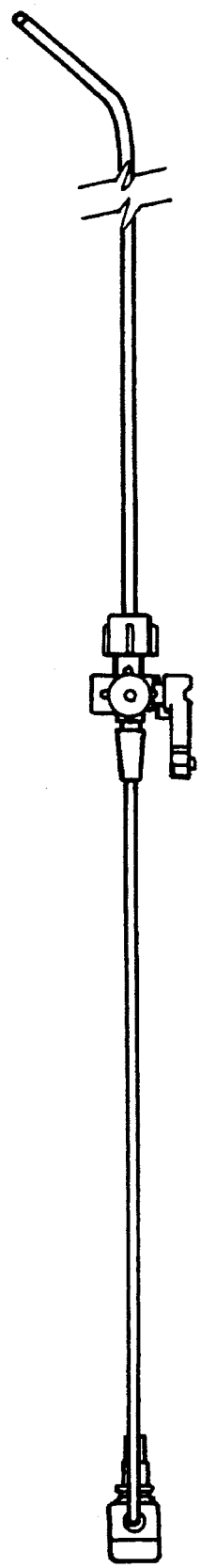
FIG. 5B is a second view of the second guiding introducer for the right atrium of FIG. 5A wherein the guiding introducer is rotated 90° clockwise from the position of FIG. 5A such that the side port tubing is positioned over a portion of the first section of the second guiding introducer.
Figure 5A:
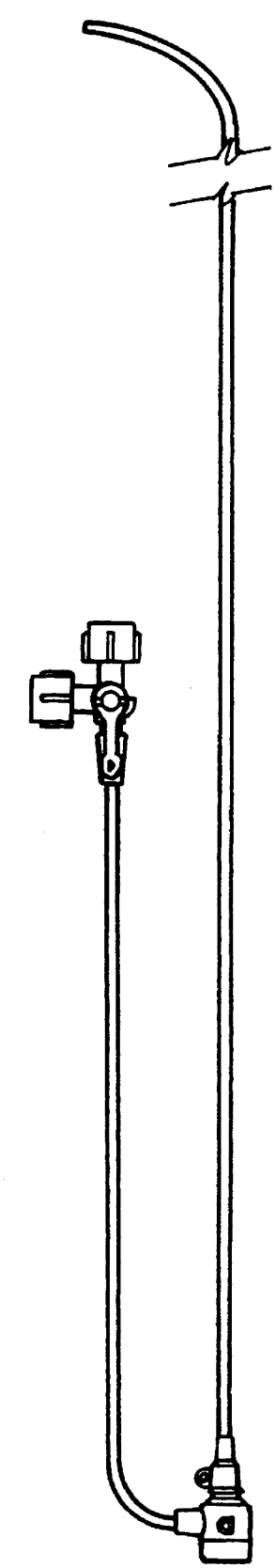
FIG. 5A is a first view of the second guiding introducer for the right atrium for use as shown in FIG. 3E to produce track 5 with the side port tubing, which is attached to the proximal end of the guiding introducer, directly to the left of the guiding introducer but generally in the same plane thereof.

The second guiding introducer for use in the right atrium is shown in FIGS. 5A and 5B. This is the same shaped guiding introducer shown in FIG. 4 in pending application Serial No. 08/147,168, assigned to a common assignee. It is designed to ablate the isthmus of tissue separating the tricuspid valve from the inferior vena cava. See FIG. 2, track 5 and FIG. 3E. Once this ablation is complete, reentry circuits are prevented from forming around the tricuspid valve or the superior and inferior vena cava. This guiding introducer is also divided into three sections. The first section is a conventional generally elongated hollow straight introducer section of sufficient length for introduction into the patient and for manipulation from the point of insertion to the specific desired location within the heart. Merged with the distal end of the first section of the guiding introducer is the second section which is curved in a compound curve curving first upward in a first curve as shown in FIG. 5B and simultaneously curving to the left in a second curve. The first longitudinal curve has a radius of from about 0.50 in. to about 2.00 in. and preferably from about 0.50 to about 1.50 in. The inner angle of the first longitudinal curve is preferably from about 140° to about 120° and preferably from about 135° to about 125°. The second longitudinal curve of the second section contains a radius from about 0.50 in. to about 4.00 in. and preferably from about 0.50 to about 2.00 in. The angle of the second longitudinal curve is preferably to the right as shown on FIG. 5A from about 70° to about 110° and preferably from about 80° to about 100°. The third section of the guiding introducer is merged with the distal end of the second section. The third section is a third curved section wherein the plane of the third section is angled upward at an angle of approximately 40° to about 60° and more preferably about 45° to about 55° from the plane of the first section wherein substantially all of the third section is coplanar. See FIGS. 5A and 5B. The arc of the curve of this third section has a radius of about 80° to about 100° and preferably from about 85° to about 95°.

Figure 6C:
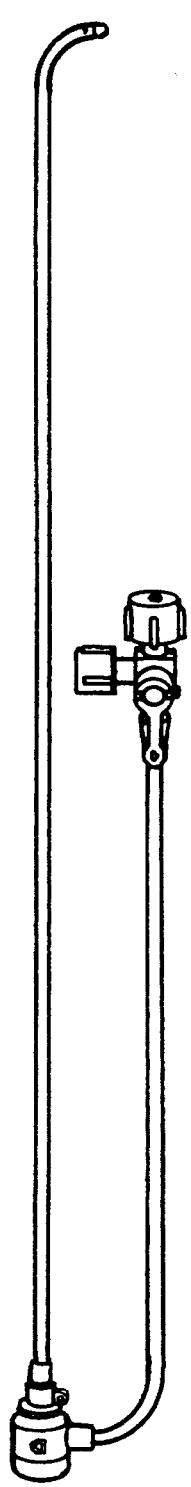
FIG. 6C is a third view of the third guiding introducer for the right atrium of FIG. 6A rotated 180° from the position of FIG. 6A such that the side port tubing is directly to the right of the guiding introducer but generally in the same plane thereof.
Figure 6B:
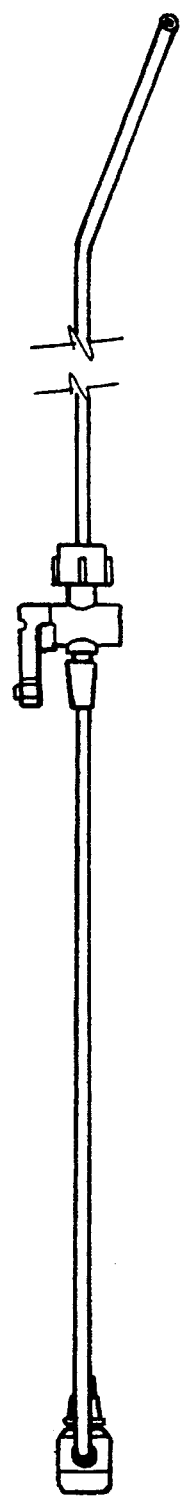
FIG. 6B is a second view of the third guiding introducer for the right atrium of FIG. 6A wherein the guiding introducer is rotated 90° clockwise from the position of FIG. 6B such that the side port tubing is positioned on top of a portion of the first section of the third guiding introducer.
Figure 6A:
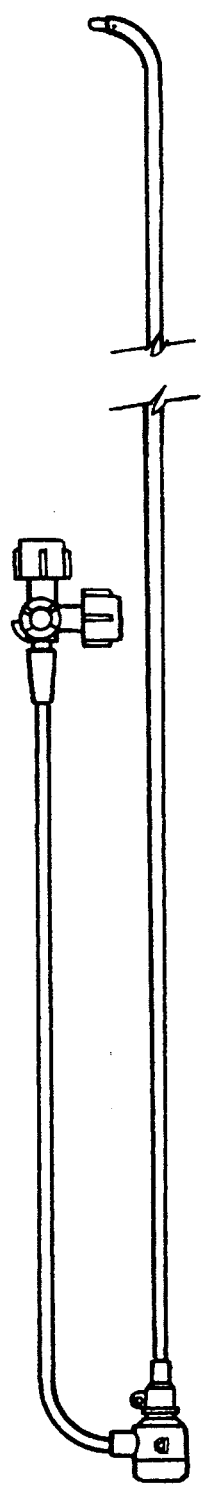
FIG. 6A is a first view of the third guiding introducer for the right atrium for use as shown in FIGS. 3F, 3G and 3H to produce tracks 6, 7 and 9 with the side port tubing, which is attached to the proximal end of the guiding introducer, directly to the left of the guiding introducer but generally in the same plane thereof.

The third ablation track in the right atrium runs along the crista terminalis around the superior and inferior vena cava. See FIG. 1, track 6 and FIG. 3F. Along with the first track in the right atrium in FIG. 1, track 5, this track is designed to prevent the formation of reentry circuits around the superior and inferior vena cava. The third right side guiding introducer to produce this ablation track also has a preferred shape. This guiding introducer is divided into three sections as shown in FIGS. 6A, 6B and 6C. (Each of the remaining guiding introducers will also be shown in three different views. In each of the views the guiding introducers will be secured to a valve for attachment to a conventional tubing and stop cock. In each such arrangement, the shape of the guiding introducer will be described making reference to its position in relation to the side port tubing where the proximal end of the guiding introducer is secured in place.) In the first of these three figures, the side port is generally in the plane of the first straight section of the guiding introducer but directed 90° to the left (see FIG. 6A). In the second drawing, the side port is rotated 90° clockwise such that the stop cock and the remaining portion of the tubing appear to cover a portion of the first section of the guiding introducer (see FIG. 6B). The third drawing (FIG. 6C) rotates the side port tubing 90° further clockwise, such that it is once again generally in the same plane as the first section of the guiding introducer but with the side port tubing on the right side of the drawing. See FIG. 6C. (Similar arrangements of the guiding introducers with the side port tubing are used with the remaining guiding introducers to assist in description.)

The first section of the third guiding introducer for the right atrium is a conventional, generally elongated hollow straight introducer section of sufficient length for introduction into the patient and for manipulation from the point of insertion to the specific desired location within the right atrium of the heart. Merged with the distal end of the first section of the second shaped, guiding introducer is a second section which is comprised of a curved section, curving to the right as shown in FIG. 6B. The inner angle of this curve is from about 170° to about 150° and preferably from about 165° to about 150°. The radius of the curve is from about 1.50 to 2.00 in. and preferably from about 1.65 to about 1.85 in. At the end of this curve begins the third section which is first a generally straight section of about 1.00 to 1.60 in. and preferably from about 1.25 to about 1.40 in. in length, concluding in a curve to the right as shown in FIG. 6C (or to the left in FIG. 6A) at an inner angle of about 70° to about 110° and preferably from about 80° to about 100°. The radius of this curve is from about 0.30 to about 0.50 in. and preferably from about 0.35 to about 0.40 in. At the end of this curve is the distal tip of the guiding introducer. Preferably the overall length of this curved section of the third section beginning at the curve and extending to the distal tip is from about 0.40 to about 0.70 in. and more preferably from about 0.50 to about 0.60 in. The distal tip of this guiding introducer may and preferably will be tapered to form a good transition with a dilator. In addition, tip markers and vents may be provided and preferably are provided near the distal tip of the guiding introducer as has been previously described.

Two additional tracks are produced in the right atrium. These are designated as tracks 7 and 9 on FIG. 1. Track 7 runs along the atrio-septal wall between the medial aspect of the superior vena cava and the inferior vena cava. This track assists in preventing the formation of reentry circuits around the superior and inferior vena cavas. The last track runs from the medial aspect of the superior vena cava near the end of the track made near the crista terminalis running anterior to the tip of the right atrial appendage. This track assists in preventing the formation of reentry circuit around the right atrial appendage. Both of these tracks can be produced either by using the first guiding introducer for the right atrium which is used to produce track 8 as shown in FIGS. 4A and 4B or the third guiding introducer for the right atrium which is used to produce the crista terminalis track designated as 6 on FIG. 1 as shown in FIGS. 6A, 6B and 6C. No additional description of these guiding introducers is necessary.

The guiding introducers for use in the left atrium will now be discussed in detail. The first guiding introducer for use in the left atrium is designed to isolate the left atrial appendage from the left pulmonary veins. Thus, the first shaped, guiding introducer is designed to assist the ablation catheter in the creation of an ablation track running from the mitral valve and the atrioventricular groove at a point anterior to the left pulmonary veins to the interatrial septum. See FIG. 2, track 1 and FIG. 3A. While preferable, all four tracks are necessary for complete ablation of reentry circuits, it is possible that relief of atrial fibrillation in the left atrium may be achieved by use of only this first track.

The first guiding introducer for use in the left atrium is preferably the same guiding introducer used to produce the ablation track 8 in the left atrium in the interatrial septum which corresponds with track 8 in the right atrium. See FIGS. 3I and 3K and FIGS. 7A, 7B and 7C.

Figure 9C:
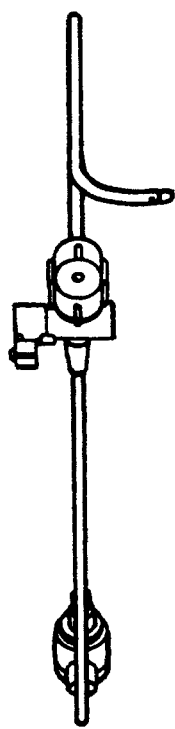
FIG. 9C is a third perspective view of the second guiding introducer for the left atrium rotated 180° from the position of FIG. 9B such that the side port tubing attached to the proximal end of the guiding introducer is positioned over a portion of the second guiding introducer for the left atrium.
Figure 9A:
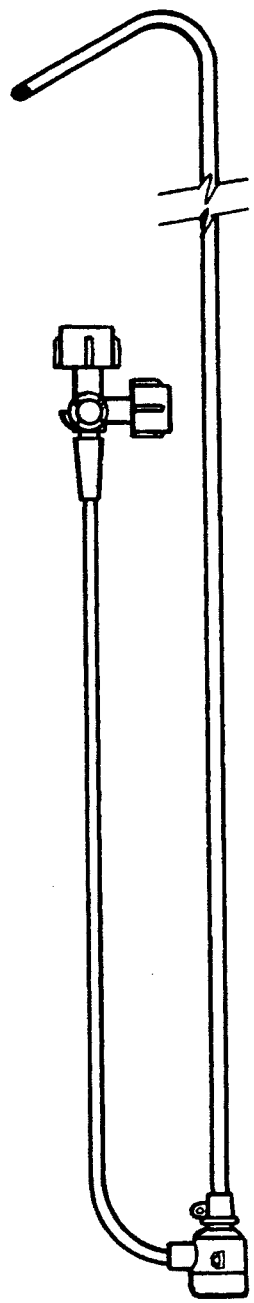
FIG. 9A is a first view of the second guiding introducer for the left atrium for use as shown in FIGS. 3B to produce track 2 with the side port tubing, which is attached to the proximal end of the guiding introducer, directly to the left of the guiding introducer and generally in the same plane thereof.
Figure 9B:
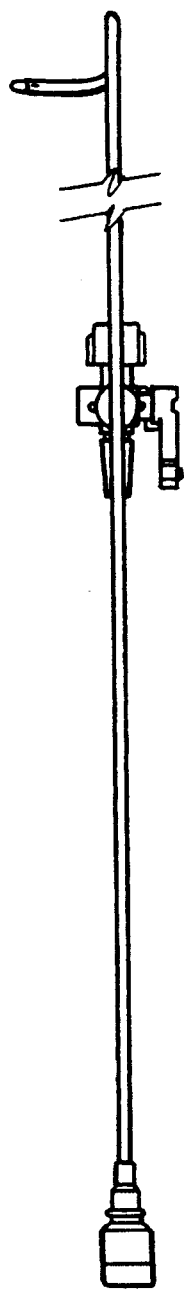
FIG. 9B is a second view of the second guiding introducer for the left atrium as shown in FIG. 9A rotated 90° counterclockwise such that the guiding introducer is positioned over the side port tubing.

The second guiding introducer for the left atrium is used to isolate the left pulmonary veins from the right pulmonary veins. See FIG. 2, track 2 and FIG. 3B. The ablation track created by use of the second guiding introducer is located roughly parallel to that of the track created by the first shaped, guiding introducer with the ablation catheter. The track runs from the mitral valve in the atrialventricular groove to the interatrial septum but between the right and left pulmonary veins. The shape of the second guiding introducer is similar to that of the first guiding introducer. The second guiding introducer is also divided into three sections. Referring now to FIGS. 9A, 9B and 9C for three views of the second guiding introducer, the first section is a conventional, generally elongated hollow, straight introducer section of sufficient length for introduction into the patient and for manipulation from the point of insertion to the specific desired location within the left atrium of the heart. Merged with the distal end of the first section of the first shaped, guiding introducer is a second section which is comprised of a curved section and a straight section. The curved section is curved to the left and downward when placed in the position shown in FIG. 9A. The inner angle of this curve is from about 40° to about 80° and more preferably from about 50° to about 70°. The radius of this curve is from about 0.30 in. to about 0.50 in. and preferably from about 0.35 in. to about 0.40 in. At the end of this curve is the straight section from about 0.50 in. to about 1.00 in. in length and preferably from about 0.70 in. to about 0.80 in. The third section of this second shaped, guiding introducer is merged with the distal end of the straight section of the second section. The third section is comprised of a curved section and a straight section. The curved section curves backward in relation to the first section when placed as shown in FIG. 9A and to the left as shown in FIG. 9B with the measure of the angle being about 80° to 100° and preferably from about 85° to 95° with a radius of about 0.25 to about 0.40 in. and preferably from about 0.30 to about 0.40 in. At the end of this curve is the short straight section whose length is from about 0.30 to about 0.70 in. and preferably from about 0.40 to about 0.60 in., ending in the distal tip of the catheter. The distal tip of this second shaped, guiding introducer may be, and preferably will be, tapered to form a good transition with a dilator as with the first guiding introducer. In addition, tip markers and vents may be provided near the distal tip of the guiding introducer as has been previously described.

Figure 10B:
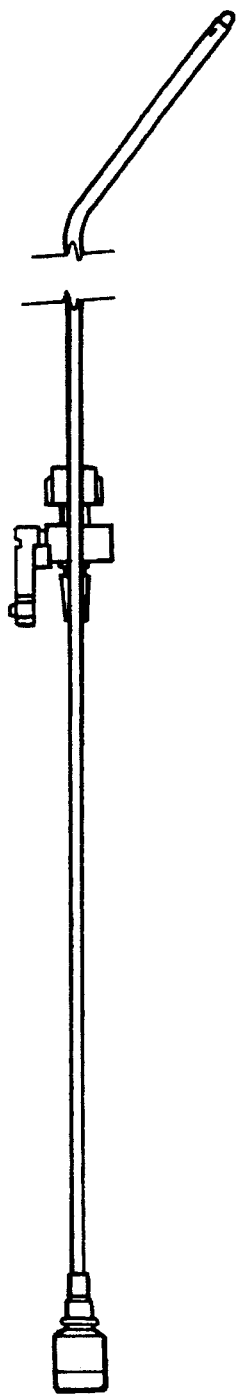
FIG. 10B is a second view of the third guiding introducer for the left atrium of FIG. 10A rotated 90° counterclockwise such that the side port tubing is behind the first section of the third guiding introducer.
Figure 10C:
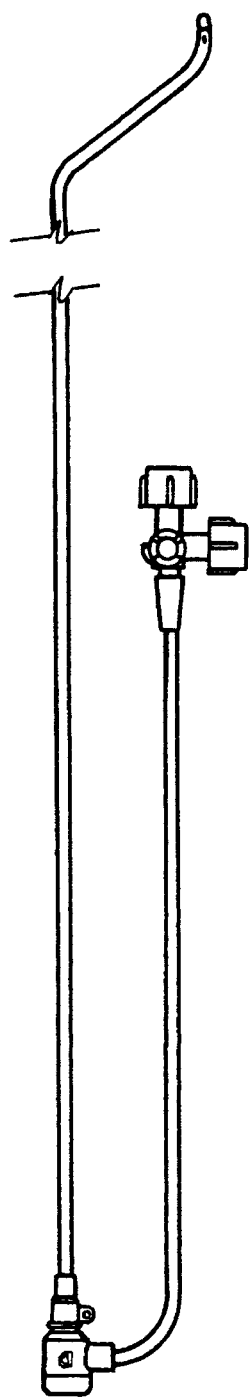
FIG. 10C is a third view of the third guiding introducer for the left atrium rotated 180° from the position shown in FIG.
Figure 10A:
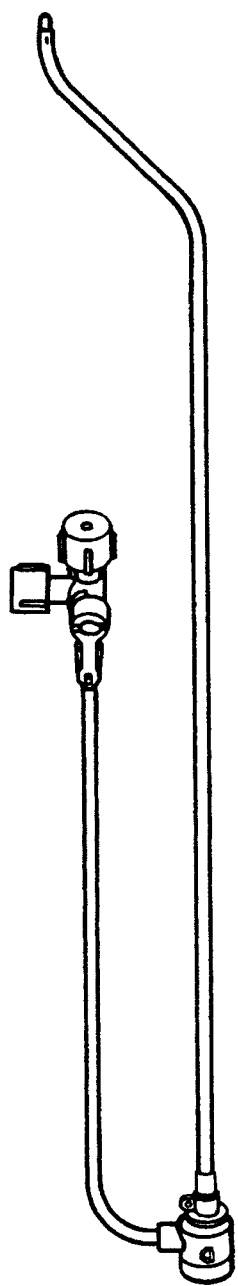
FIG. 10A is a first view of the third guiding introducer for the left atrium for use as shown in FIG. 3C to produce track 3 with the side port tubing, which is attached to the proximal end of the guiding introducer, directly to the left of the guiding introducer and generally in the same plane thereof.

Referring now to FIGS. 10A, 10B and 10C for three different views, the third guiding introducer for use in the left atrium has a significantly different shape than the first two guiding introducers for the left atrium. It is specifically designed to complete the isolation of the left interior pulmonary vein and surrounding tissue from the remaining portion of the left atrium. See FIG. 2, track 3 and FIG. 3C. It is designed to assist in the creation of an ablation track running from a point superior and lateral from the left inferior pulmonary vein and extends between the left pulmonary veins to intersect with the tracks created by the ablation catheters when used with the first and second guiding introducers for the left atrium.

The third guiding introducer is comprised of a first, second and third section. See FIGS. 10A, 10B and 10C. The first section of this third guiding introducer is a conventional generally elongated hollow, straight introducer section of sufficient length for introduction and for manipulation from the point of insertion to the specific desired location within the left atrium. Merged with the distal end of the first section is the second section which is comprised of a compound curve and a straight section. The compound curve of the second section is curved first to the left in a first curve in relation to the first straight section, as shown in FIG. 10A and simultaneously curving backward in relation to the first section in a second curve (or to the right as shown in FIG. 10B). The first curve has a radius of about 0.40 in. to about 0.60 in. and preferably from about 0.45 to about 0.55 in. The inner angle of the first curve is preferably from about 155° to about 115° and preferably from about 140° to about 120°. The second curve of this second section has a radius of about 0.15 to about 0.45 in. and preferably from about 0.20 to about 0.30 in. The inner angle of this second curve is from about 120° to about 160° and preferably from about 130° to about 150°. The straight portion of this second section of this third guiding introducer begins at the end of this compound curve and is about 1.20 in. to about 1.50 in. and preferably from about 1.30 to about 1.50 in. in length. At the end of this straight section begins the third section which is comprised of a curved section and a straight section. The curved section curves at an inner angle of about 155° to about 115°, preferably about 140° to about 120° as shown in FIG. 10A and has a radius of about 0.40 to about 0.60 in. This curve is in the same plane as the straight portion of the second section. At the end of this curve is the straight section ending in the distal tip of the guiding introducer. This straight section is relatively short, preferably about 0.20 to about 0.40 cm. Preferably, it is tapered to form a good transition with a dilator. As with the other guiding introducers, radiopaque tip marker bands may be used as well as preferably vents near the distal tip.

The fourth guiding introducer for the left atrium is specifically designed for use in the left atrium to isolate the right inferior pulmonary vein from the right superior pulmonary vein. It is designed to assist in the creation of an ablation track running from the posterior aspect of the interatrial septum, anterior between the right superior and inferior pulmonary veins to intersect the second track. See FIG. 2, track 4 and FIG. 2D.

The shape of the fourth guiding introducer is different from that of the first three guiding introducers for the left atrium and is comprised of a first, second and third sections. See FIGS. 11A, 11B and 11C for three different views. The first section is a conventional generally elongated hollow, straight section of sufficient length for introduction into the patient and for manipulation from the point of insertion to the specific desired location within the left atrium. Merged with the distal end of this first section is the second section which is comprised of a compound curved section and a straight section. The compound curved section curves first to the left in relation to the first section as shown in FIG. 11A in a first curve and simultaneously curves backward away from the first section (or to the right as shown in FIG. 11B) in a second curve. The first curve has an inner angle of about 155° to about 105°, preferably from about 140° to about 120° with a radius of about 0.25 to about 0.50 in. and preferably from about 0.30 to about 0.40 in. The second curve has an inner angle of about 155° to about 125° and preferably from about 150° to about 130° with a radius of about 0.30 to about 0.70 in. and preferably from about 0.40 to about 0.60 in. At the end of the compound curved section of the second section is the straight section of the second section of the fourth guiding introducer which is from about 1.00 to about 2.00 in. and preferably from about 1.20 to about 1.50 in. in length. At the end of this straight section is the third section, which is comprised of a curved section ending in the distal tip of the guiding catheter. The curved section curves to the left in an arc from the plane of the first section as shown in FIG. 11A at an inner angle of about 40° to about 80° and preferably from about 50° to about 70° with a radius of about 0.30 to about 0.50 in. and preferably from about 0.35 to about 0.40 in. As with the first, second and third guiding introducers for the left atrium, radiopaque tip marker bands may be used as well as preferably vents near the distal tip of the fourth guiding introducer.

The combined effect of these four ablation tracks along with the ablation track along the interatrial septum will be the segregation of the left atrium into five discreet sections that do not directly communicate electrically with each other. Specifically, the small section of tissue around the left inferior pulmonary vein is isolated from the remaining portions of the left atrium. However, each of the other sections are able to undergo electrical activity or contraction moderated by the prevailing sinus rate. Based on experimental data and sensing operations, the number of ablation procedures may be reduced or increased.

While the preferred procedure in the left atrium creates five tracks, additional track may be necessary, especially if the heart is enlarged. Alternatively, fewer ablation procedures may be necessary under some circumstances depending on the needs of the particular patient.

Ablation procedures in the left atrium alone may be adequate to relieve the symptom of atrial arrhythmia. If so, no ablation procedures may be necessary in the right atrium. However, for the effective ablation of atrial fibrillation, ablation procedures should also occur in the right atrium.

In operation, a modified Seldinger technique is normally used for the insertion of the guiding introducers and ablation catheters into the body. Using this procedure, a small skin incision is made at the appropriate location to facilitate the catheter or dilator passage. Subcutaneous tissue is then dissected, followed by a puncture of the vessel with an appropriate needle with stylet positioned at a relatively shallow angle. The needle is then partially withdrawn and reinserted at a slightly different angle into the vessel making sure that the needle remains within the vessel. The soft flexible tip of an appropriate size guidewire is then inserted through, and a short distance beyond, the needle into the vessel. Firmly holding the guidewire in place, the needle is removed. The guidewire is then advanced through the vessel into the right femoral vein and through the inferior vena cava into the right atrium. (The preferred procedure uses the inferior approach to the right and left atria. Procedures for the retrograde and superior approach to the left atrium and superior approach to the right atrium can also be used. However, the shapes of the guiding introducers must be modified to adjust for the alternative approach.) With the wire guide in place, the dilator is then placed over the wire with the first guiding introducer to be used placed over the dilator. The dilator and this guiding introducer generally form an assembly to be advanced together along the guidewire into the inferior vena cava. After insertion of the assembly, the guidewire is then withdrawn.

The first guiding introducer for use in the right atrium is then passed over the guidewire to perform ablation and mapping procedures in the right atrium. The purpose of the ablation tracks in the right atrium is to prevent the formation of reentry circuits around the superior and inferior vena cava and the tricuspid valve, as well as to isolate the right atrial appendage. In the preferred procedure, the ablation tracks in the right atrium are first produced prior to production of the ablation track of the left atrium. See FIG. 1. While the order of ablation of the tracks in the right atrium is not critical, the preferred order of the tracks as shown in FIG. 1 is track 5, 6, 7, 9 and 8. Several passes along each track may be necessary to achieve complete ablation. Sensing catheters can also be used in the right atrium to assure that complete ablation has been accomplished. Once it has been determined that adequate ablation has occurred, the last guiding introducer for the right atrium is removed to complete the process for the treatment of atrial arrhythmia in the right atrium.

After the procedures are completed in the right atrium, the last right side guiding introducer is removed and a Brockenbrough needle or trocar is then inserted through the lumen of the dilator to the right atrium to be used to create an opening through the interatrial septum, preferably at the fossa ovalis. (This procedure is used for insertion of the guiding introducers into the left atrium. The penetration of the interatrial septum will preferably be performed prior to completion of the right atrium procedures to permit the formation of a specific ablation track (See FIG. 2, track 8) in the left atrium at the same time the parallel track (FIG. 1, track 8) is formed in the right atrium. The entire assembly (dilator and Brockenbrough needle) passes through the vena cava into the right atrium so that the tip rests against the interatrial septum at the level of the fossa ovalis. The Brockenbrough needle is then advanced within the dilator to reach the fossa ovalis. After an opening is made through the interatrial septum, the needle, dilator and first guiding introducer for the left atrium are advanced into the left atrium. After the first guiding introducer for the left atrium is advanced through the interatrial septum into the left atrium, the Brockenbrough needle and dilator are removed leaving the first guiding introducer in the left atrium. The ablation catheter is then advanced through the lumen of the guiding introducer and is placed at the location within the left atrium which is created by the unique shape of the first guiding introducer. The choice of the guiding introducer to be used will depend on the procedure to be used by the medical practitioner. Several passes across each preferred track may be necessary to effectively ablate the entire track. In the preferred procedure the four ablation guiding introducers are used in sequence one through four (see FIG. 2 and FIGS. 3A, 3B, 3C and 3D) to produce tracks 1, 2, 3 and 4 in order. Obviously, modifications in the sequence of use of the guiding introducers can be made by the medical practitioners. When disconnecting the ablation source from the ablation catheter and connecting the catheter to the sensing equipment, a separate electrophysiology sensing catheter may be used with one or more of the shaped guiding introducers to sense or map locations within the left atrium to determine whether an adequate ablation track has been created. As previously discussed, the procedure in the left atrium is designed to segregate the left atrium into five discreet segments that do not directly communicate with each other, but do communicate with the S.A. node. In addition, it is designed to segregate the tissue around the left interior pulmonary vein from all of the remaining tissue of the left atrium. By this procedure discreet pathways or corridors are created which will prevent or limit the formation of reentry circuits within the left atrium. While the location of specific tracks may change depending on the conditions of the individual heart, the general procedure as set forth above is the preferred procedure to achieve the results desired for the left atrium.

By choice of the desired guiding introducer in coordination with fluoroscopic viewing, the distal portion of the appropriate guiding introducer can be manipulated to direct the distal end of the mapping and/or ablation catheter which is placed within the lumen of the guiding introducer to a specific surface within the left or right atrium. In addition, by providing sufficient rigidity and support, as the guiding introducer is held in place by the various anatomical structures of the heart, as well as the vascular surfaces, the distal end of the guiding introducer can be maintained at that fixed location or surface position of the endocardial structure to permit the appropriate ablation. The precise location of the ablation catheter tip is important as there will be no dilution of the energy delivered due to the unfocused energy being dissipated over the entire cardiac chamber and lost in the circulating blood by a constantly moving tip of the ablating catheter. This permits a significantly reduced amount of energy to be applied during the ablation procedure. Further, time used to perform the procedure is significantly reduced over procedures where no guiding introducer is used. In addition, by this ablation procedure the same types of destruction of the discrete tracks can be achieved as have been accomplished, for example, in surgical applications such as by use of the "Maze" procedure, the corridor procedure and other such surgical procedures.

It will be apparent from the foregoing that while particular forms of the invention have been illustrated and described, various modifications can be made without departing from the spirit and scope of the invention. Accordingly, it is not intended that this invention be limited except as by the appended claims.

We claim:

1. A process for the treatment of atrial arrhythmia within the atria of a human heart by use of ablation and mapping procedures whereby said procedures comprise introducing into the atria a precurved, guiding introducer, wherein said introducer contains a proximal and a distal end and a lumen running within said guiding introducer from proximal to distal ends, introducing into said lumen of said guiding introducer an ablation and mapping catheter, guiding the catheter to a selected area of the atria by use of the guiding introducer, wherein a portion of said catheter extends out the distal end of the lumen of the guiding introducer, and mapping and ablating the selected area of the atria by use of the catheter thereby producing an ablation track.

2. The process of claim 1 wherein the selected area for the ablation is within the left atrium.

3. The process of claim 2 wherein the left atrial appendage is isolated from the pulmonary veins.

4. The process of claim 2 wherein five guiding introducers are utilized for the ablation procedures in the left atrium.

5. The process of claim 1 wherein the selected area for the ablation is within the right atrium.

6. The process of claim 1 wherein the selected area is within the left atrium and the right atrium.

7. The process of claim 1 wherein the selected area for ablation comprises a plurality of tracks in the left atrium.

8. The process of claim 7 wherein the ablation of the plurality of tracks results in the following:

(a) isolation of the left atrial appendage from the pulmonary veins;

(b) isolation of the left pulmonary veins from the right pulmonary veins;

(c) isolation of the left interior pulmonary vein from the left superior pulmonary vein; and (d) isolation of the right interior pulmonary vein from the right superior pulmonary vein.

9. The process of claim 8 wherein five guiding introducers are utilized for the ablation procedures in the left atrium.

10. The process of claim 1 wherein the selected area for ablation comprises a plurality of tracks in the right atrium.

11. The process of claim 10 wherein the area for ablation within the right atrium comprises tracks around the superior vena cava to the inferior vena cava and between the inferior vena cava and the tricuspid valve.

12. The process of claim 1 wherein the selected area for ablation comprises a plurality of tracks in the left atrium and the right atrium.

13. The process of claim 1 wherein pharmacological procedures are utilized along with the ablation procedures to assist in the treatment of atrial arrhythmia.

14. The process of claim 1 wherein the ablation procedures utilize one of the following: direct current, radio frequency, microwave, ultrasound, laser procedures, and fulgutronization procedures as the source for the ablation.

15. The process of claim 14 wherein the ablation procedures are performed utilizing radio frequency energy.

16. The process of claim 1 wherein noncurved guiding introducers, as well as the precurved, guiding introducer are utilized in conjunction with the catheter to assist in the treatment of atrial arrhythmia.

17. The process of claim 1 wherein the guiding introducer is tapered at the distal end.

18. The process of claim 1 wherein the guiding introducer has vent holes near a distal tip of the guiding introducer.

19. A process for the treatment of atrial arrhythmia which includes the use of ablation and mapping procedures comprising
   (a) introducing a precurved, right atrium guiding introducer into the right atrium of a human heart, wherein said guiding introducer contains a proximal and distal ends and a lumen running within said guiding introducer from proximal to distal ends;
   (b) positioning a mapping and ablation catheter within the right atrium using the right atrium guiding introducer, wherein a portion of said catheter extends out the distal end of the lumen of the guiding introducer;
   (c) mapping and ablating a preselected track within the right atrium by use of the ablation and mapping catheter and the right atrium guiding introducer;
   (d) repeating steps a, b and c as needed using the same or a different precurved, right atrium guiding introducer to ablate and map one or more selected tracks within the right atrium;
   (e) introducing a precurved, left atrium guiding introducer into the left atrium of a human heart, wherein said guiding introducer contains a proximal and distal ends and a lumen running within said guiding introducer from proximal to distal ends;
   (f) positioning an ablation and mapping catheter within the left atrium using the left atrium guiding introducer, wherein a portion of said catheter extends out the distal end of the lumen of the guiding introducer;
   (g) mapping and ablating a preselected track within the left atrium by use of the ablation and mapping catheter and the left atrium guiding introducer;
   (h) repeating steps e, f and g as needed using the same or different guiding introducers to ablate one or more preselected tracks within the left atrium, thereby creating a generally uninterrupted pathway for electrical impulses from the sinoatrial node to the atrioventricular node while also permitting atrial contraction mediated by the SA node, as well as enhanced atrioventricular synchrony.

20. The process of claim 19 wherein the preselected track within the left atrium isolates the left atrial appendage from the pulmonary veins.

21. The process of claim 19 wherein the preselected tracks within the left atrium
   (a) isolate the left atrial appendage from the pulmonary veins,
   (b) isolate the left pulmonary veins from the right pulmonary veins,
   (c) isolate the left interior pulmonary vein from the left superior pulmonary vein, and
   (d) isolate the right interior pulmonary vein from the right superior pulmonary vein.

22. The process of claim 7 wherein the left interior pulmonary vein is isolated from the remaining portion of the left atrium.

23. The process of claim 19 wherein the ablation and mapping procedure in the left atrium creates four separate tracks designed to divide the left atrium into five discreet sections wherein the first track will extend from the atrioventricular groove at a point anterior to the left pulmonary vein to the interatrial septum, wherein the second track will extend from the interatrial septum to the atrioventricular groove on a course between the right and left pulmonary veins, wherein the third ablation track will extend from a point superior and lateral from the left interior pulmonary vein and extending between the left pulmonary veins to intersect with the second track, and wherein the fourth track will extend from the posterior aspect of the interatrial septum anterior between the right superior and inferior pulmonary veins to intersect the second track.

24. The process of claim 23 wherein a fifth track is created, directed to extend from the fossa ovalis, superior to the septal roof along the interatrial septum.

25. The process of claim 19 wherein ablation tracks in the right atrium are made around the superior vena cava to the inferior vena cava and between the inferior vena cava and the tricuspid valve.

26. The process of claim 19 wherein the ablation tracks in the right atrium comprise a first track along the crista terminals around the superior and inferior vena cava, a second track directed at the tissue separating the tricuspid valve from the inferior vena cava and a third track along the atrio-septal wall between the superior vena cava and the inferior vena cava.

27. The process of claim 26 wherein a fourth track is produced directed from the medial aspect of the superior vena cava at the crista terminalis track anterior to the right atrial appendage.

28. The process of claim 27 wherein a fifth track is created, designed to extend from the fossa ovalis, superior to the septal roof along the interatrial septum.

29. A process for the treatment of atrial arrhythmia within the atria of a human heart by use of ablation and mapping procedures whereby said procedures comprise
   introducing into the atria a precurved, guiding introducer, wherein said introducer contains a proximal and a distal end,
   introducing into said guiding introducer an ablation and mapping catheter,
   guiding the catheter to a selected area of the atria by use of the guiding introducer, wherein the selected area for ablation comprises a plurality of tracts in the left atrium, and
   mapping and ablating the selected area of the atria by use of the catheter, thereby producing an ablation track.

30. The process of claim 29 wherein the left atrial appendage is isolated from the pulmonary veins.

31. The process of claim 29 wherein the ablation of the plurality of tracks results in the following:
   (a) isolation of the left atrial appendage from the pulmonary veins;
   (b) isolation of the left pulmonary veins from the right pulmonary veins;
   (c) isolation of the left interior pulmonary vein from the left superior pulmonary vein; and
   (d) isolation of the right interior pulmonary vein form the right superior pulmonary vein.

32. The process of claim 31 wherein five guiding introducers are utilized for the ablation procedures in the left atrium.

33. The process of claim 29 wherein noncurved guiding introducers, as well as precurved, guiding introducers may be utilized in conjunction with the ablation catheter to assist in the treatment of atrial arrhythmia.

34. The process of claim 29 wherein five guiding introducers are utilized for the ablation procedures in the left atrium.

35. The process of claim 29 wherein the guiding introducer has vent holes near the distal end of the guiding introducer.

36. A process for the treatment of atrial arrhythmia within the atria of a human heart by use of ablation and mapping procedures whereby said procedures comprise introducing into the atria a precurved, guiding introducer, wherein said introducer contains a proximal and a distal end, introducing into said guiding introducer an ablation and mapping catheter, guiding the catheter to a selected area of the atria by use of the guiding introducer, wherein the selected area for ablation comprises a plurality of tracks in the right atrium, and mapping and ablating the selected area of the atria by use of the catheter.

37. The process of claim 36 wherein the area for ablation within the right atrium comprises tracks around the superior vena cava to the inferior vena cava and between the inferior vena cava and the tricuspid valve.

38. The process of claim 36 wherein noncurved guiding introducers, as well as precurved, guiding introducers may be utilized in conjunction with the ablation catheter to assist in the treatment of atrial arrhythmia.

39. The process of claim 36 wherein the guiding introducer has vent holes near the distal end of the guiding introducer.

40. A process for the treatment of atrial arrhythmia within the atria of a human heart by use of ablation and mapping procedures whereby said procedures comprise introducing into the atria a precurved, guiding introducer, wherein said introducer contains a proximal and a distal end, introducing into said guiding introducer an ablation and mapping catheter, guiding the catheter to a selected area of the atria by use of the guiding introducer, wherein the selected area for ablation comprises a plurality of tracks in the left atrium and the right atrium, and mapping and ablating the selected area of the atria by use of the catheter.

41. The process of claim 40 wherein noncurved guiding introducers, as well as precurved, guiding introducers may be utilized in conjunction with the ablation catheter to assist in the treatment of atrial arrhythmia.

42. The process of claim 40 wherein the guiding introducer has vent holes near the distal end of the guiding introducer.

* * * * *